(12) United States Patent
Akahoshi et al.

(10) Patent No.: US 9,040,294 B2
(45) Date of Patent: May 26, 2015

(54) PLASMID VECTOR, METHOD FOR DETECTING GENE PROMOTER ACTIVITY, AND ASSAY KIT

(75) Inventors: Eiichi Akahoshi, Tokyo (JP); Mitsuko Ishihara, Tokyo (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/593,912

(22) Filed: Aug. 24, 2012

(65) Prior Publication Data

US 2013/0230872 A1 Sep. 5, 2013

(30) Foreign Application Priority Data

Aug. 25, 2011 (JP) ................. 2011-183896

(51) Int. Cl.
*C12N 15/00* (2006.01)
*C12Q 1/68* (2006.01)
*C12N 15/69* (2006.01)
*C12N 15/85* (2006.01)

(52) U.S. Cl.
CPC .............. *C12Q 1/6897* (2013.01); *C12N 15/69* (2013.01); *C12N 15/85* (2013.01)

(58) Field of Classification Search
None
See application file for complete search history.

(56) References Cited

U.S. PATENT DOCUMENTS

| | | | |
|---|---|---|---|
| 5,283,179 A * | 2/1994 | Wood ................................. | 435/8 |
| 6,410,314 B1 | 6/2002 | Baiker et al. | |
| 2009/0142841 A1 * | 6/2009 | Occhiodoro et al. ......... | 435/455 |
| 2011/0010244 A1 | 1/2011 | Hatridge et al. | |
| 2011/0244471 A1 | 10/2011 | Akahoshi et al. | |
| 2012/0077203 A1 | 3/2012 | Ishihara et al. | |

FOREIGN PATENT DOCUMENTS

| | | | |
|---|---|---|---|
| WO | WO 98/07876 A2 | | 2/1998 |
| WO | WO 98/07876 A3 | | 2/1998 |
| WO | WO 2005005644 A1 | * | 1/2005 |
| WO | WO 2009/038841 A2 | | 3/2009 |

OTHER PUBLICATIONS

DiMaio et al., Journal of Molecular Biology, 1982, vol. 156 pp. 531-548.*
Soneoka et al., Nucliec Acids Research, 1995, vol. 23, pp. 628-633.*
Makrides et al., Micorbiological Reviews, 1996, vol. 60, pp. 512-538.*
Murine polyomavirus, Genbank, 2010, retrieved on Dec. 14, 2013 from: http://www.ncbi.nlm.nih.gov/nuccore/NC_001515.1.*
Mittal et al., Virology, 1995, vol. 210, pp. 226-230.*
Martinez-Salas, Current Opinion in Biotechnology, 1999, vol. 10, pp. 458-464.*
Bhattacharyya et al., Journal of Virology, 1995, vol. 69, pp. 7579-7585.*
Choi et al., Glycoconjugate Journal, 2005, vol. 22, pp. 63-69.*
U.S. Appl. No. 13/429,926, filed Mar. 26, 2012, Akahoshi, et al.
Toru Kojima, et al., The Journal of Clinical Investigation, "A simple biological imaging system for detecting viable human circulating tumor cells", vol. 119, No. 10, Oct. 2009.
Extended European Search Report Issued Nov. 26, 2012 in Patent Application No. 12181691.2.
Claudia Argueta et al., "Construction and use of GFP reporter vectors for analysis of cell-type-specific gene expression in *Nostoc punctiforme*", Journal of Microbiological Methods, vol. 59, No. 2, XP004563768, Nov. 1, 2004, pp. 181-188.
Tatsuo Muramatsu et al., "Effect of Self-Replication DNA Sequences of Epstein-Barr Virus on the Expression of a Foreign Gene Transfected In Vivo to the Mouse Testis", Anim. Sci. Technol. (Jpn.), vol. 68, No. 7, XP002687073, 1997, pp. 650-653.

* cited by examiner

*Primary Examiner* — Michele K Joike
*Assistant Examiner* — Mindy G Brown
(74) *Attorney, Agent, or Firm* — Oblon, McClelland, Maier & Neustadt, L.L.P.

(57) ABSTRACT

According to one embodiment, a first gene encodes a reporter protein. The first gene is disposed at the downstream of the gene promoter. A second gene is disposed at the downstream of the gene promoter and encodes a replication origin-binding protein. An internal ribosome entry site is disposed between the first gene and the second gene. The transcription termination signal sequence encodes a signal for terminating the transcription of the first gene and the second gene. A replication origin sequence is recognized by the replication origin-binding protein.

19 Claims, 8 Drawing Sheets

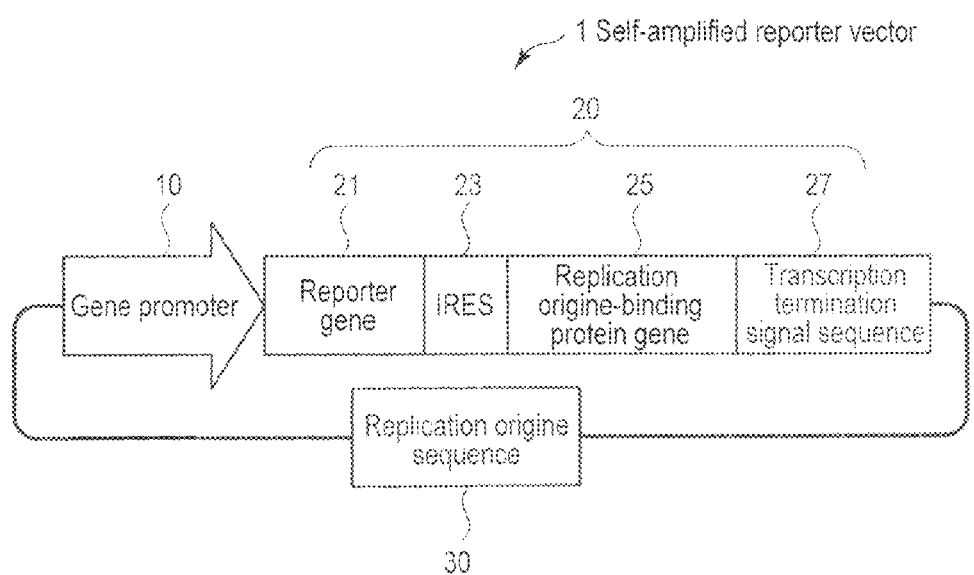
F I G. 1

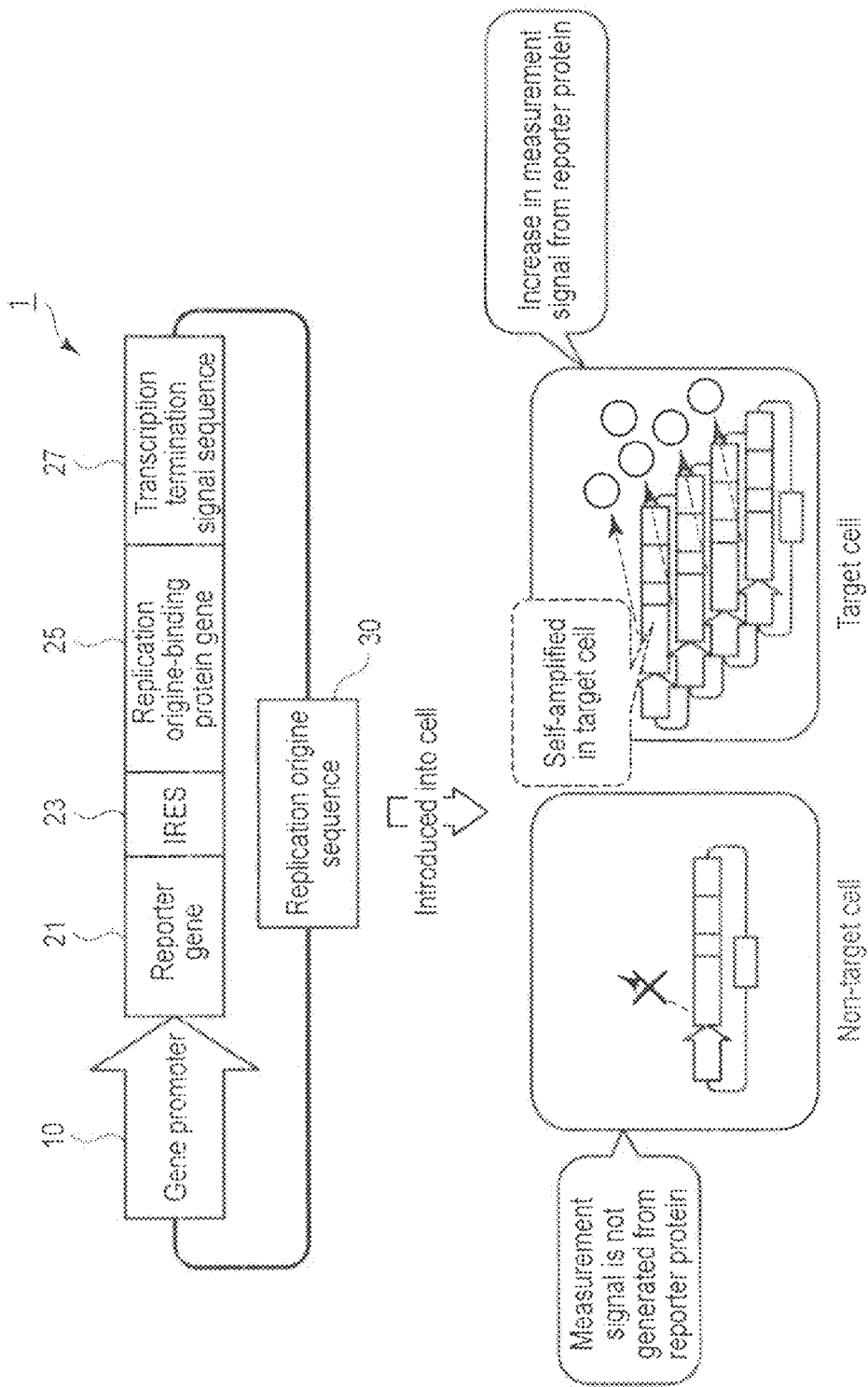
F I G. 2

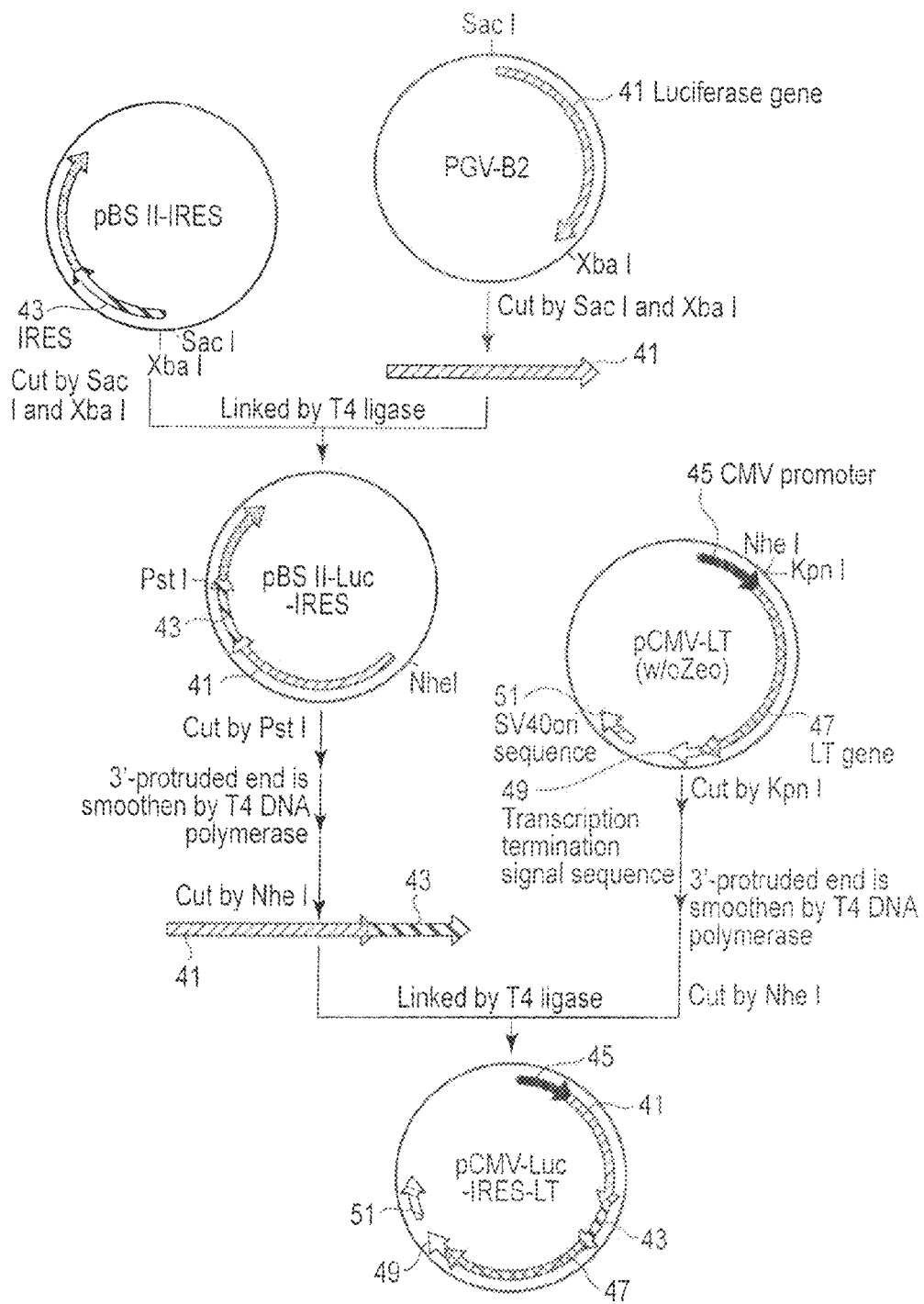
F I G. 3

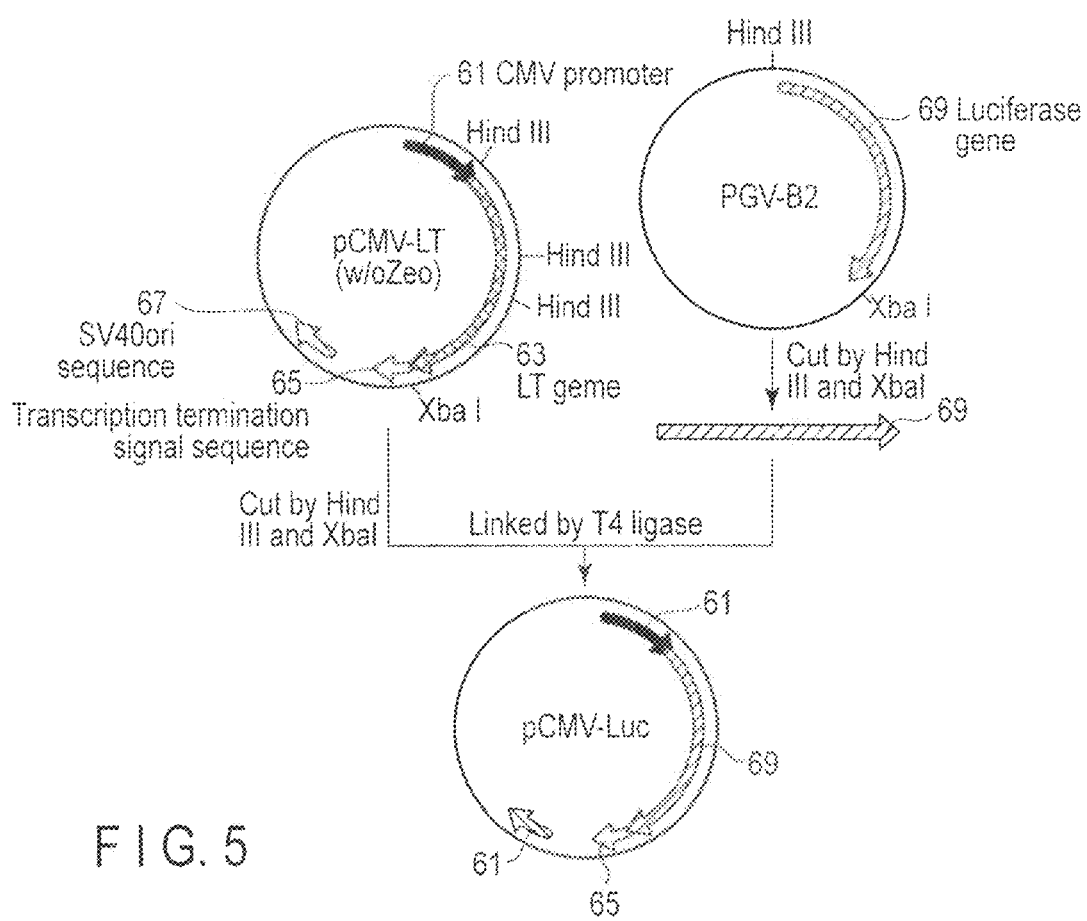
F I G. 5
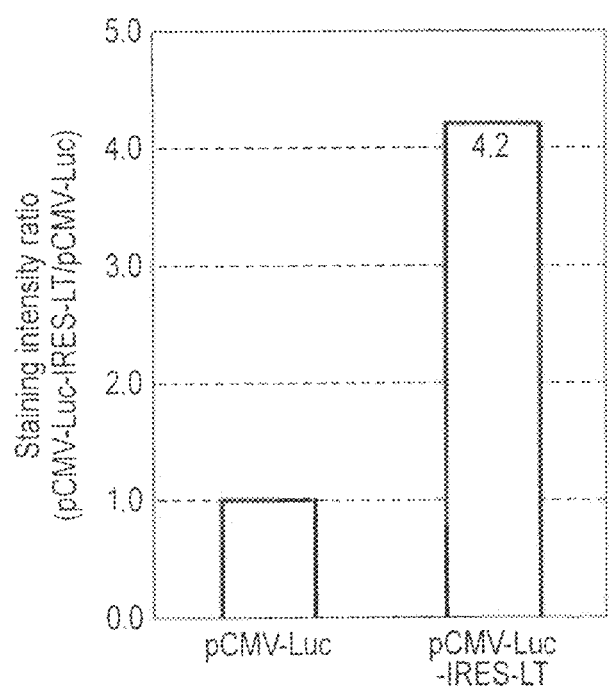
F I G. 7B

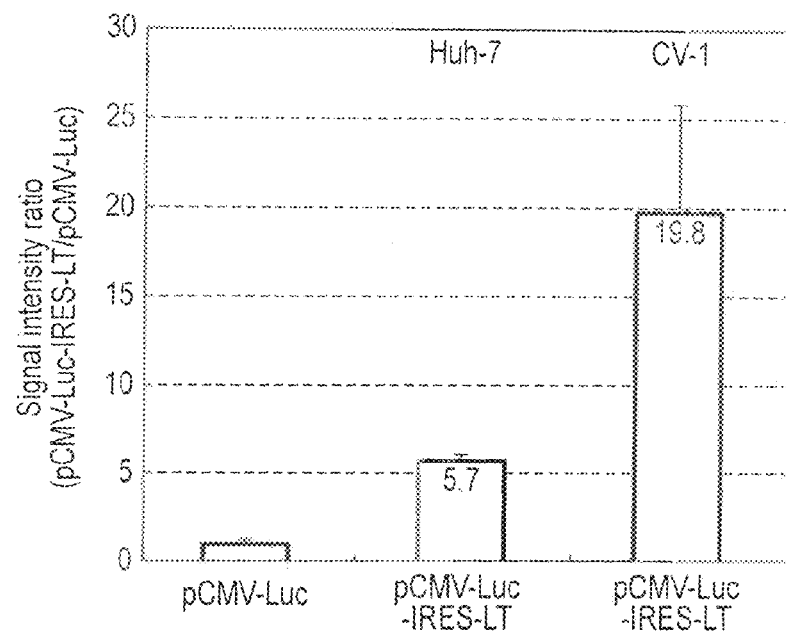
F I G. 8
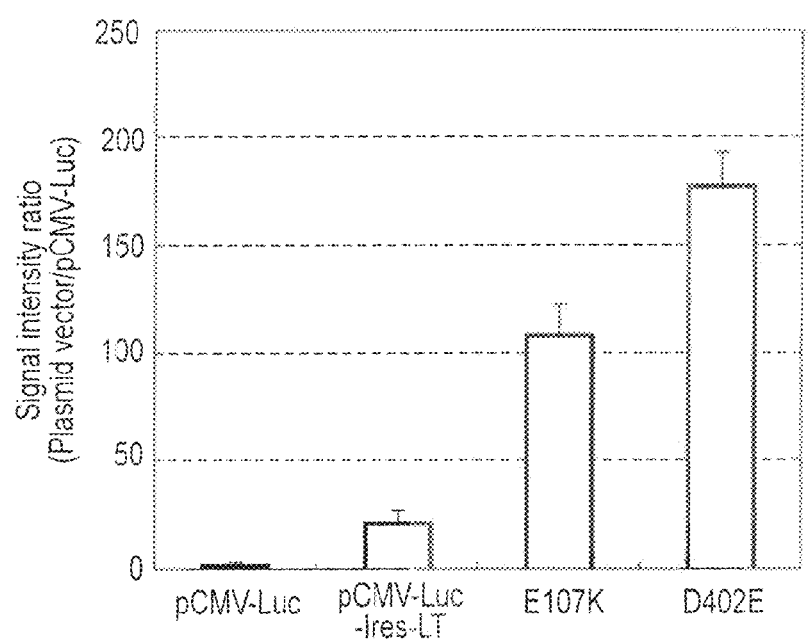
F I G. 9

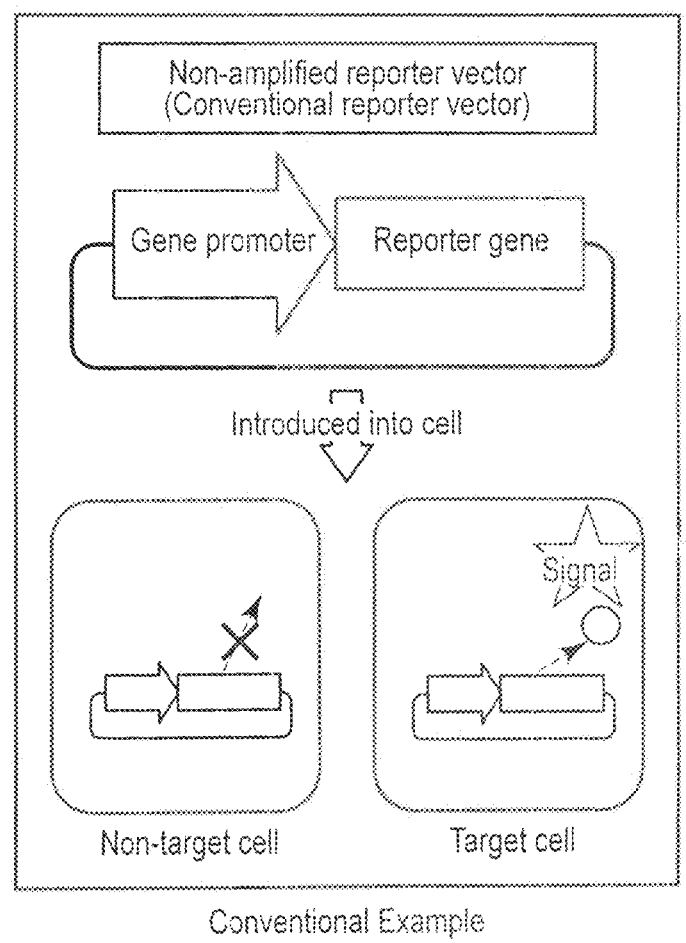
F I G. 10

PLASMID VECTOR, METHOD FOR DETECTING GENE PROMOTER ACTIVITY, AND ASSAY KIT

CROSS-REFERENCE TO RELATED APPLICATIONS

This application is based upon and claims the benefit of priority from Japanese Patent Application No. 2011-183896, filed Aug. 25, 2011, the entire contents of which are incorporated herein by reference.

FIELD

Embodiments described herein relate generally to a plasmid vector, a method for detecting the activity of a gene promoter, and an assay kit.

BACKGROUND

Development of a novel method for the diagnosis of a disease based on genome information has been expected since the base sequence of the human genome was determined. For example, genes relating to various diseases such as cancers have been found from gene analyses based on the base sequence information of genomes. These disease-related genes and disease-related proteins are attracting attentions as diagnostic bio-markers for diseases such as cancers. However, under the current circumstance, a stable result cannot be obtained by a diagnosis by detecting a bio-marker, for the reasons that sufficient expression of the bio-marker cannot be necessarily obtained at an early stage of a disease, and the like.

Early diagnosis of diseases is essential for the future medical treatments from the viewpoints of improvement in cure rates and reduction of the burden by patients. As an approach for early diagnosis, a method comprising detecting the change in the promoter activity of a gene that expresses at an early stage of a disease. The probability of expression of the gene is controlled by the change in the activity of a gene promoter. The activity of gene promoters is observed earlier than the expression of disease-related genes and disease-related proteins.

As a method for detecting the activity of a gene promoter in a cell, a reporter gene assay may be exemplified. The reporter gene assay is a method comprising introducing a reporter vector in which an expression cassette to which a reporter gene for visualizing the activity of a promoter is bound is incorporated at the downstream of the promoter into a subject cell, and quantifying the activity of the promoter based on the activity of a reporter protein. As the reporter gene, a luciferase gene, a (β-galactosidase gene, a fluorescent protein gene and the like are adopted.

However, for example, at an early stage of a disease, the number of cell in a pre-disease state by the change in the activity of a gene promoter is quite little. It cannot be considered that the probability of incorporation of the cell in blood or a tissue collected for diagnosis is high. Therefore, a technique for detection with high sensitivity is required for early diagnosis of a disease and the like.

At present, as a reporter gene assay with high sensitivity, a method by a virus reporter vector in which a gene promoter and a fluorescent protein are incorporated in a genome of a virus has been reported. In this reporter gene assay, the sensitivity of the reporter gene assay is increased by increasing the amount of expression of the fluorescent protein by proliferating a virus vector in a host cell infected with the virus vector, thereby increasing the amount of expression of the fluorescent protein. However, a virus reporter vector utilizes the ability of infection of a virus for introducing the vector into a host cell. Therefore, there is a risk of infection of an operator with the virus reporter vector. Accordingly, the handling of the virus reporter vector is not convenient, and there is a problem in safeness.

On the other hand, a plasmid reporter vector is handled more conveniently than the virus reporter vector is, and has no infectiveness and has high safeness. Many reporter gene assays using a plasmid reporter vector have been reported. An application of a plasmid reporter vector to early diagnosis of diseases is expected. However, unlike a virus reporter vector, a plasmid vector does not proliferate in a host cell, and thus there is a problem in the detection sensitivity thereof.

The object of the embodiment is to provide a plasmid vector, a method for detecting a gene promoter and an assay kit, by which the activity of a gene promoter can be detected with high sensitivity.

BRIEF DESCRIPTION OF THE DRAWINGS

FIG. 1 is a drawing that schematically shows the structure of the plasmid vector according to the present embodiment;

FIG. 2 is a drawing that shows the whole image of a method for detecting the activity of a gene promoter (a reporter gene assay) using the plasmid vector of FIG. 1;

FIG. 3 is a drawing that schematically shows a typical flow of the method for preparing the plasmid vector according to the present embodiment pCMV-Luc-IRES-LT;

FIG. 5 is a drawing that schematically shows a typical flow of a method for preparing the vector pCMV-Luc for a negative control according to the present embodiment;

FIG. 7B is a drawing showing the result of the comparison of the copy numbers of the pCMV-Luc-IRES-LT and pCMV-Luc according to examples of the present embodiment, which shows a graph (a graph of a staining intensity ratio of the bands in FIG. 7A) for the comparison of the copy numbers of the pCMV-Luc-IRES-LT and pCMV-Luc;

FIG. 8 is a drawing that shows the results of the detection of the light emission signals of the reporter protein in the pCMV-Luc-IRES-LT and pCMV-Luc according to examples of the present embodiment;

FIG. 9 is a drawing that shows the result of the comparison of the signal intensities of the reporter protein in the pCMV-Luc-IRES-LT, pCMV-Luc-IRES-LT-E107K and pCMV-Luc-IRES-LT-D402E according to examples of the present embodiment with the pCMV-Luc; and FIG. 10 is a drawing that shows the whole image of the method for detecting the activity of a gene promoter using a non-amplified reporter vector according to a conventional example.

DETAILED DESCRIPTION

Figure 4:
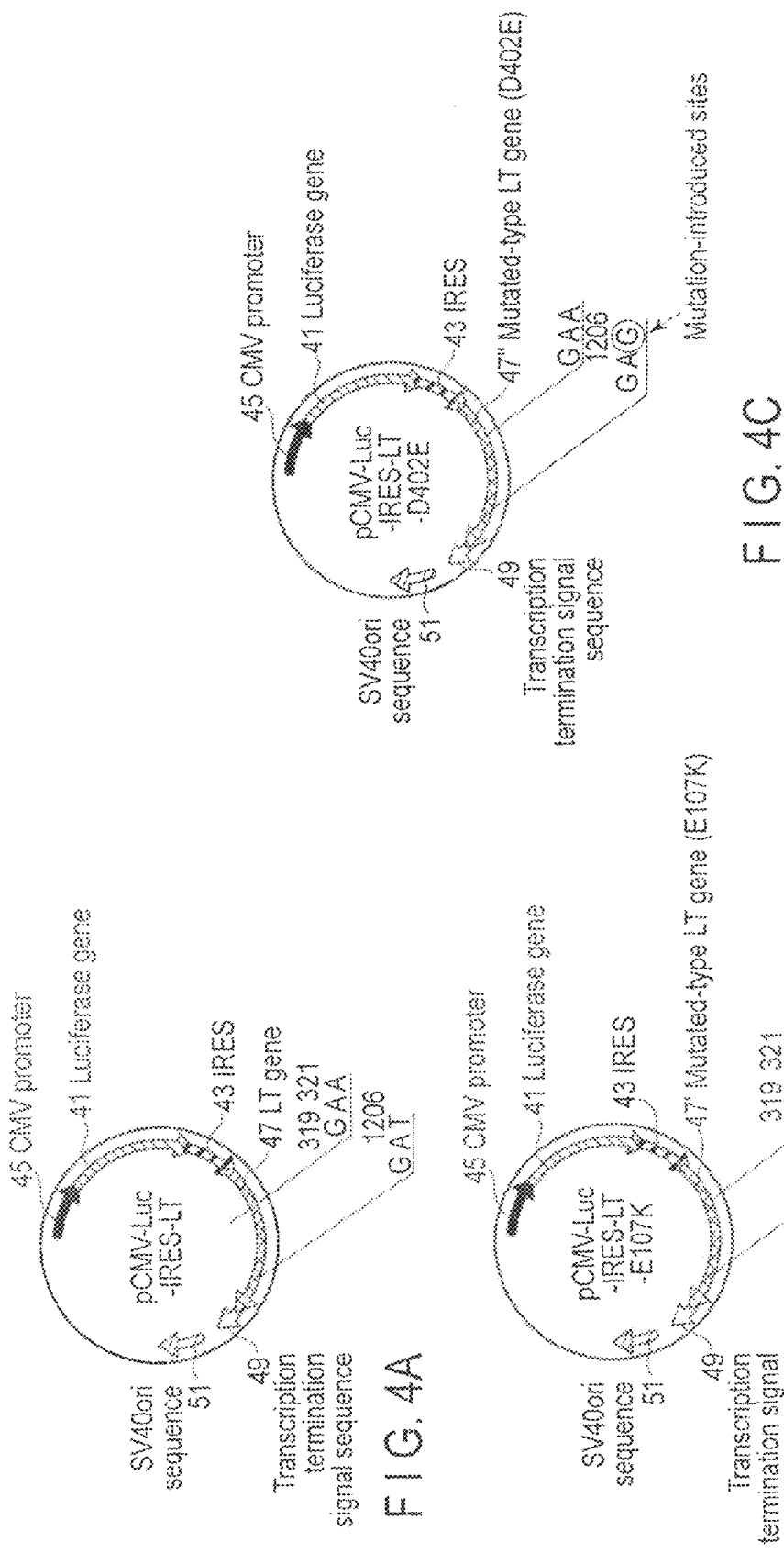
FIG. 4A is a drawing that schematically shows the structure of the pCMV-Luc-IRES-LT according to an example of the present embodiment.
FIG. 4B is a drawing that schematically shows the structure of the pCMV-Luc-IRES-LT-E107K according to an example of the present embodiment.
FIG. 4C is a drawing that schematically shows the structure of the pCMV-Luc-IBES-LT-D402E according to an example of the present embodiment.

In general, according to one embodiment, a plasmid vector includes a gene promoter, a first gene, a second gene, an internal ribosome entry site, a transcription termination signal sequence and a replication origin sequence. The first gene encodes a reporter protein for visualizing the activity of the gene promoter which is disposed at the downstream of the gene promoter. The second gene is disposed at the downstream of the gene promoter and encodes a replication origin-binding protein. The internal ribosome entry site is disposed between the first gene and the second gene. The transcription termination signal sequence encodes a signal for terminating the transcription of the first gene and the second gene. The replication origin sequence is recognized by the replication origin-binding protein.

Hereinafter the plasmid vector, the method for detecting a gene promoter, and the assay kit according to the present embodiment will be explained with referring to drawings.

The plasmid vector according to the present embodiment is a plasmid-type reporter vector that enhances a detection signal by the specific self-amplification of a gene promoter to be detected in an activated host cell.

[Structure of Plasmid Vector]

FIG. 1 is a drawing that schematically shows the structure of the plasmid vector 1 that is a self-amplified reporter vector according to the present embodiment. As shown in FIG. 1, the plasmid vector 1 according to the present embodiment has a gene promoter 10 to be detected. A base sequence 20 for transcription and translation is disposed at the downstream of the gene promoter 10 to be detected. The base sequence 20 includes a reporter gene 21, an internal ribosome entry site (IRES) 23, a replication origin-binding protein gene 25 and a transcription termination signal sequence 27. The IRES 23 is disposed between the reporter gene 21 and the replication origin-binding protein gene 25. The transcription termination signal sequence 27 is disposed at the downstream of the replication origin-binding protein 25. Furthermore, the plasmid vector 1 has a replication origin sequence 30 at the sites other than the site between the gene promoter 10 and the transcription termination signal sequence 27 at the side that the reporter gene 21 and the replication origin-binding protein gene 25 go through. Although it is explained that the reporter gene 21 is disposed at the upper stream of the IRES 23 and the replication origin-binding protein gene 25 is disposed at the downstream, the present embodiment is not limited to this. For example, the replication origin-binding protein gene 25 may be disposed at the upper stream of the IRES 23 and the reporter gene 21 may be disposed at the downstream. In this case, it is preferable that the transcription termination signal sequence 27 is disposed at the downstream of the reporter gene 21.

Hereinafter the individual elements included in the plasmid vector 1 will be explained in detail.

The gene promoter 10 to be detected is a base sequence having a binding sequence of an RNA polymerase. The gene promoter 10 activates the transcription of a gene that is functionally bound to a binding sequence of an RNA polymerase. An arbitrary gene promoter may be used for the gene promoter 10 depending on the intended purpose. For example, if early diagnosis of a disease is intended, an arbitrary disease-related gene promoter that has been activated at the early stage of the disease can be used as the gene promoter 10. Specifically, in the case when the disease is a cancer, gene promoters such as c-fos, c-myc, CD13, CD44, CD90, Snail and drug resistant transporter genes (ABCG, MDR), and the like can be utilized as the gene promoter 10. If detection of an environmental stimulus such as harmful chemical substances, temperatures and oxidation stress is intended, a gene promoter that is activated in response to the intended environmental stimulus can be used as the gene promoter 10. Specifically, in the case when the environmental stimulus is a harmful chemical substance, a gene promoter of cytochrome p450 or the like can be utilized as the gene promoter 10. In addition, the gene promoter 10 may include an arbitrary enhancer. An enhancer is a base sequence that is linked to the gene promoter 10. The enhancer has a function of enhancing the activation of the transcription of a gene by the gene promoter 10.

The reporter gene 21 is a gene (base sequence) that encodes a reporter protein. The reporter gene 21 has a role to visualize the activity of the gene promoter 10. As the reporter gene 21, all of reporter genes that are already known in the art can be applied. As the reporter gene 21, a reporter gene that can easily measure the activity of a reporter protein that is a translation product of the reporter gene and provides a low measurement background is preferable. Specific examples of the reporter gene 21 may include a luminescent enzyme gene, a fluorescent protein gene, a color-developing enzyme gene, an active oxygen-generating enzyme gene, a heavy metal-binding protein gene and the like. The reporter gene 21 can be suitably selected depending on an apparatus for detecting a reporter protein.

The replication origin-binding protein gene 25 is a gene that encodes a replication origin-binding protein. The replication origin-binding protein is a protein that may function to origin the replication of a DNA in a host cell. The replication origin-binding protein may be, for example, a protein derived from a virus that is amplified by infection with a host cell, or a protein of the same animal species as that of a host cell or a protein of a different animal species from that of a host cell.

The IRES 23 is a base sequence for transcripting the reporter gene 21 and the replication origin-binding protein gene 25 to a single mRMA (a bicistronic mRMA) so that a reporter protein that is a translation product of the reporter gene 21 and a replication origin-binding protein that is a translation product of the replication origin-binding protein gene 25 can be synthesized individually. More specifically, the IRES 23 is a base sequence that initiates the translation of a protein by binding a ribosome to the inside of an mRNA without depending on the 5'-end cap structure of the mRNA in a mammal cell. By disposing the IRES 23 between the two genes, a bicistronic mRNA is synthesized. Namely, by incorporating the IRES 23 between the two genes, two kinds of proteins that are encoded by these two genes are translated in one mRNA. Examples of the IRES 23 may include an IRES of encephalomyocarditis virus (ECMV), and the like. The IRES 23 according to the present embodiment is disposed between the reporter gene 21 and the replication origin-binding protein gene 25 to link the reporter gene 21 to the replication origin-binding protein gene 25. Therefore, a reporter protein and a replication origin-binding protein are translated from one bicistronic mRNA.

The transcription termination signal sequence 27 is a base sequence that encodes a signal for terminating the transcription of the reporter gene 21 and the replication origin-binding protein gene 25 at the upper stream. The transcription termination signal sequence 27 may be one that functions to terminate the transcription of a gene of a mammal. Examples of the transcription termination signal sequence 27 may include a late poly (A) addition signal sequence of Simian Virus 40 (SV40), a poly (A) addition signal sequence of bovine growth hormone gene, and the like. However, the transcription termination signal sequence 27 according to the present embodiment is not limited to these signal sequences. As long as the functions of a transcription termination signal sequence are not impaired, these signal sequences whose gene sequences have been modified may also be used as the transcription termination signal sequence 27.

A replication origin sequence 30 is a base sequence that can be recognized by a replication origin-binding protein that is synthesized by the expression of the replication origin-binding protein gene 25. The replication of the plasmid vector 1 is initiated by the recognition of and binding to the replication origin sequence 30 by the replication origin-binding protein. The replication origin sequence 30 may be one derived from the same origin as that of the animal species of the replication origin-binding protein, or may be one derived from a different origin.

For example, in the case when the plasmid vector 1 is introduced into a cell of a primate such as a human and a simian, a large T antigen (LT) gene of SV40 can be used as the replication origin-binding protein gene 25, and an on sequence of SV40 can be used as the replication origin sequence 30. Alternatively, in the case when the plasmid vector 1 is introduced into a cell of a primate such as a human and a simian, an EBNA-1 protein of Epstein-Barr virus (EBV) can be used as the replication origin-binding protein gene 25, and an EB virus latent origin of replication (oriP) can be used as the replication origin sequence 30. Furthermore, in the case when the plasmid vector 1 is introduced into a cell of a rodent such as a mouse, a large T antigen (LT) gene of Mouse polyomavirus (PyV) can be used as the replication origin-binding protein gene 25, and a PyV core origin sequence can be used as the replication origin sequence 30.

As mentioned above, the plasmid vector 1 according to the present embodiment comprises the reporter gene 21, the replication origin-binding protein 25 and the replication origin sequence 30 in the same vector. By doing so, the plasmid vector 1 according to the present embodiment functions as a self-amplified reporter vector.

[Detection of Activity of Gene Promoter]

The method for detecting the activity of the gene promoter 10 according to the present embodiment (a reporter gene assay) detects the activity of the gene promoter 10 to be detected by using the plasmid vector (a self-amplified reporter vector) 1 according to the present embodiment.

FIG. 2 is a drawing that shows the whole image of a reporter gene assay using the plasmid vector according to the present embodiment.

As shown in FIG. 2, the plasmid vector 1 is first introduced into a host cell. As the method for introducing the plasmid vector 1 into the host cell, an already-known cell engineering technique is used. For example, as the method for introducing the plasmid vector 1 into the host cell, a biochemical method or a physicochemical method is used. Examples of the biochemical method may include a lipofection method using a cation lipid, a magnetofection method using magnetic particles, and a method using calcium chloride, and the like. Examples of the physicochemical method may include an electroporation method, a sonoporation method, and the like. As the method for introducing the plasmid vector 1 into the host cell, the above-mentioned biochemical methods and physicochemical methods may be used alone or in combination. For example, the lipofection method and magnetofection method which are biochemical methods may be combined, or the lipofection that is a biochemical method and an electroporation method that is a physicochemical method may be combined.

After the plasmid vector 1 has been introduced into the host cell, the host cell is cultured over an arbitrary period under a culture condition in which the host cell can divide and proliferate. This culture condition is a condition in which the plasmid vector 1 can be amplified. In this culture period, in the case when the state of the host cell or the environment in which the host cell is placed satisfies the activation condition that is inherent to the gene promoter 10, the gene promoter 10 is activated. Thus, in the case when the gene promoter 10 is in an activated state in a host cell that satisfies the activation condition (target cell), the reporter gene 21 and the replication origin-binding protein gene 25 which have been linked in the IRES 23 are transcribed to a bicistronic mRNA and translated. By these transcription and translation, a reporter protein (a signal to be measured) and a replication origin-binding protein are synthesized. The replication origin-binding protein recognizes and binds the replication origin sequence 30 and recruits plural proteins relating to the replication of DNAs included in the host cell (a DNA replication apparatus). The plasmid vector 1 is replicated in the host cell by the recruited plural proteins. By this way, the plasmid vector 1 repeats replication one after another in the host cell and amplifies a copy number. In accordance with the amplification of a copy number, the number of reporter proteins synthesized by the plasmid vector 1 is also increased.

On the other hand, in the case when the host cell does not satisfy the activation condition of the gene promoter 10, the gene promoter 10 is not activated. In a host cell that does not satisfy the activation condition (a non-targeted cell), the reporter gene 21 and the replication origin-binding protein gene 25 are not transcripted and translated. Therefore, a reporter protein and a replication origin-binding protein are not synthesized. In this case, a measurement signal is not generated in the non-targeted cell. Since a replication origin-binding protein is not synthesized, the plasmid vector 1 cannot conduct replication.

By this way, the plasmid vector 1 according to the present embodiment is self-amplified only in a host cell (target cell) that satisfies the activation condition of the gene promoter 10. Next, a conventional plasmid vector (non-amplified reporter vector) shown in FIG. 10 will be considered. A conventional plasmid vector does not have a replication origin-binding protein and a replication origin sequence, and thus cannot be self-amplified even in a target cell. Therefore, the plasmid vector 1 according to the present embodiment can increase the signal of a reporter protein in a target cell, i.e., an object to be measured, as compared to the conventional plasmid vector. Therefore, the sensitivity of the reporter gene assay can be increased.

Hereinafter the detection of the amount of expression of the reporter protein will be explained in detail. As mentioned above, a luminescent enzyme gene, a fluorescent protein gene, a color-developing enzyme gene, an active oxygen-generating enzyme gene, a heavy metal-binding protein gene or the like can be selected as the reporter gene 21.

The luminescent enzyme gene is a gene that encodes an enzyme protein that catalyzes a luminescent reaction. Examples of the luminescent enzyme gene may include a luciferase gene. Luciferase is a translation product of the luciferase gene. Luciferase conducts a luminescent reaction by using luciferin that is one of the substrates thereof.

The fluorescent protein gene is a gene that encodes a fluorescent protein. Examples of the fluorescent protein gene may include a blue fluorescent protein gene, a green fluorescent protein gene and a red fluorescent protein gene. The blue fluorescent protein that is a translation product of the blue fluorescent protein gene emits blue fluorescence. The green fluorescent protein that is a translation product of the green fluorescent protein gene emits green fluorescence. The red fluorescent protein that is a translation product of the red fluorescent protein gene emits red fluorescence.

The color-developing enzyme gene is a gene that encodes an enzyme protein that catalyzes a color-development reaction. Examples of the color-developing enzyme gene may include a β-galactosidase gene. β-galactosidase that is a translation product of the β-galactosidase gene conducts a color development reaction by using a substrate such as 5-bromo-4-chloro-3-indolyl-β-D-galactopyranoside (X-Gal) and o-nitrophenyl-β-D-galactopyranoside (ONPG).

The translation products of the luminescent enzyme gene, fluorescent protein gene and color-developing enzyme gene can be detected by an optical detection apparatus. Specifically, in the case when the reporter gene 21 is a luciferase gene, a luciferase protein is extracted from a host cell, and a substrate is added to the extracted luciferase protein. The luminescence intensity of the solution comprising the luciferase protein and substrate is measured by a luminometer. In the case when the reporter gene is a fluorescent protein gene, for example, a host cell is irradiated with laser. By the irradiation of laser, fluorescence is generated from the fluorescent protein in the host cell. The intensity of the generated fluorescence is measured by a fluorophotometer. Alternatively, in the case when the reporter gene is a fluorescent protein gene, the intensity of fluorescence may be measured as follows. First, an extraction liquid comprising the fluorescent protein extracted from the host cell is irradiated with laser. By the irradiation of laser, fluorescence is generated from the fluorescent protein in the extraction liquid. The intensity of the fluorescence is measured by a fluorophotometer. In the case when the reporter gene is a β-galactosidase gene, a β-galactosidase protein is extracted, and a substrate is added to the extracted β-galactosidase protein. The absorbance of the solution comprising the β-galactosidase protein and substrate is measured by an absorbance measurement apparatus.

The active oxygen-generating enzyme gene is a gene that encodes an enzyme that generates active oxygen. Examples of the active oxygen-generating enzyme gene may include a nitric monoxide synthase gene, a xanthine oxidase gene and the like. Nitric monoxide synthase that is a translation product of the nitric monoxide synthase gene and xanthine oxidase that is a translation product of the xanthine oxidase gene generate active oxygen.

Active oxygen can be detected by an electron spin resonance (ESR) apparatus. In a method by the ESR apparatus, the amount of generation of active oxygen may be measured directly, or may be measured by utilizing a specific spin trap agent. In the case when the spin trap agent is utilized, at first, an active oxygen-generating enzyme is trapped by the spin trap agent. Then, the amount of generation of the active oxygen generated from the trapped active oxygen-generating enzyme is measured by the ESR apparatus.

The heavy metal-binding protein gene is a gene that encodes a protein that specifically binds to a heavy metal. The amount of generation of the protein bound to the heavy metal can be measured by a diagnostic imaging apparatus such as a magnetic resonance imaging (MRI) apparatus, a positron emission computed tomography (PET) apparatus and a computed tomography (CT) apparatus. For example, the amount of generation of the heavy-metal-binding protein is conducted as follows. First, a heavy metal that can be measured is added to a culture liquid of a host cell. The host cell is then washed, and a heavy-metal-binding protein is extracted from the host cell. An image of the extracted heavy-metal-binding protein is then photographed by an image diagnosis apparatus that corresponds to the heavy metal added to the culture liquid. The image diagnosis apparatus generates an image relating to the heavy-metal-binding protein. In the image diagnosis apparatus, the generated image is subjected to an image processing and the amount of the heavy-metal-binding protein is measured. The heavy-metal-binding protein may be expressed inside of the host cell, or may be expressed on the outer surface of the host cell.

In the case when a gene that encodes a protein that binds a ferromagnetic metal such as iron, gadolinium or a complex compound thereof is utilized as the heavy metal-binding protein gene, a nuclear magnetic resonance apparatus such as an MRI apparatus is preferable as the image diagnosis apparatus. In this case, the heavy metal-binding protein gene may be an antibody gene or single-strand antibody gene that specifically binds to a ferromagnetic metal such as the above-mentioned complex compounds. Specifically, as the heavy metal-binding protein gene, ferritin and transferrin which are iron-binding proteins, or single-strand antibodies having an ability of binding to gadolinium are suitable.

In the case when a gene that encodes a protein that binds a radioactive isotope metal such as strontium, copper, technetium, gallium or complex compounds thereof is utilized as the heavy metal-binding protein gene, a radiation measurement apparatus such as a PET apparatus and a CT apparatus is preferable as the image diagnosis apparatus. In this case, an antibody gene or single-strand antibody gene that specifically binds to a radioactive isotope metal such as the above-mentioned complex compounds may be used as the heavy metal-binding protein gene.

Thus, according to the reporter gene assay according to the present embodiment, the amount of expression of the reporter protein from the plasmid vector 1 can be measured by a detection apparatus corresponding to the reporter protein. Furthermore, the presence or absence of the activity of the gene promoter 10 can be detected by the comparison of the measured value and threshold value of the amount of expression by utilizing a detection apparatus. For example, in the case when the measured value of the amount of expression is larger than a threshold value, it is considered that the activity of the gene promoter 10 is detected, and in the case when the measured value of the amount of expression is smaller than the threshold value, it may be considered that the activity of the gene promoter 10 is not detected. The threshold value can optionally be set by a user depending on the gene promoter 10, the reporter gene 21, the host cell and the like.

As mentioned above, the gene promoter 10 can be suitably selected depending on an object to be detected. For example, in the case of diagnosis of a cancer, it is preferable that a gene promoter of a cancer-related gene such as c-fos, c-myc, CD13, CD44, CD90, Snail and drug-resistant transporter genes (ABCG, MDR) is used as the gene promoter 10. By doing so, the plasmid vector 1 is amplified in a cancer cell and the amount of expression of the reporter protein is increased, and thus the cancer cell included in the host cell can be detected with high sensitivity. As another example, in the case of detection of an environmental stimulus, it is preferable to use a environment-specific promoter as the gene promoter 10. Therefore, by providing a desired environmental stimulus such as a chemical substance, a temperature and an oxidation stress to the host cell, the plasmid vector 1 is amplified in the cell and the amount of expression of the reporter protein is increased, and thus the environmental stimulus can be detected with high sensitivity.

Furthermore, as a cell that can be used as the host cell, cells derived from primates including human and simians, rodents such as mice and rats, and the like can be applied. Furthermore, established cell lines and primacy cultured cells can also be applied as these cells. Examples of established cell lines that are derived from primates may include Huh-7 and HepG2 derived from human hepatic cancer, Jurkat and HL60 derived from human blood corpuscle cells, MCF-7 derived from human breast cancer and CV-1 derived from simian kidney, or subclones and genetically modified cells thereof, and the like. Examples of established cell lines derived from rodents may include Hepa-1 derived from murine hepatic cancer, Neuro2a derived from murine neuroblastoma, PC12 derived from rat pheochromocytoma, or subclones and genetically modified cells thereof, and the like. Examples of the primacy cultured cells may include cells and tissue stem cells which are derived from organs of the digestive system including liver, lungs, kidneys and the like, the circulation system including leucocytes and the like, the endocrine system including thyroid gland and the like, or the central nerve system including brain, spinal cord and the like, and the like.

The host cell used in the reporter gene assay according to the present embodiment may be selected depending on the kinds of the replication origin-binding protein gene 25 and replication origin sequence 30 which are incorporated into the plasmid vector 1. For example, in the case when the replication origin-binding protein gene 25 is an LT protein gene of SV40 and the replication origin sequence 30 is SV40ori, or in the case when the replication origin-binding protein gene 25 is an EBNA-1 protein of EBV and the replication origin sequence 30 is oriP of EBV, it is preferable to select a cell derived from a primate such as a human and a simian as the host cell. Furthermore, in the case when the replication origin-binding protein gene 25 is an LT protein of PyV and the replication origin sequence 30 is a PyV core origin sequence, it is preferable to select a cell derived from a rodent such as a mouse as the host cell.

The kind of the cell is not specifically limited as long as the combination of the plasmid vector 1 and the animal species of the host cell is correct. For example, the host cell may also be a established cell line or a primary cultured cell. Furthermore, the tissue from which the host cell is derived is also not specifically limited. This may be selected depending on the kind of the gene promoter 10 to be detected.

Thus, by using the plasmid vector 1 according to the present embodiment, a method for detecting the activity of the gene promoter 10 with high sensitivity, i.e., a highly-sensitive reporter gene assay can be provided.

[Assay Kit]

The assay kit according to the present embodiment is used in the reporter gene assay according to the present embodiment.

The assay kit according to the present embodiment has the plasmid vector 1 according to the present embodiment and a detection reagent. The detection reagent is a reagent for detecting the expression of the reporter gene 21 that encodes the reporter protein included in the plasmid vector 1 in the cell. Furthermore, the assay kit according to the present embodiment may further have an introduction reagent and an extraction reagent. The introduction reagent is a reagent for introducing the plasmid vector 1 into a cell. The extraction reagent is a reagent for extracting the reporter protein from the cell. Furthermore, the assay kit according to the present embodiment may include a reaction cuvette and a cell culture vessel. The reaction cuvette is a cuvette for conducting a reaction by the detection reagent, introduction reagent and extraction reagent. The cell culture vessel is a vessel for culturing the host cell to which the plasmid vector 1 has been introduced. Furthermore, the assay kit according to the present embodiment may further comprise a culture medium for culturing and a buffer.

Thus, the assay kit according to the present embodiment can detect the activity of the gene promoter 10 with high sensitivity by being used in the reporter gene assay according to the present embodiment.

EXAMPLES

1. Base Sequence of Plasmid Vector

Next, the plasmid vector according to the present embodiment will be explained with referring to cases when a cell of a primate such as a human and a simian is used as a host cell as specific examples. As the plasmid vector 1 in these specific examples, pCMV-Luc-IRES-LT is adopted. An LT gene of SV40 is adopted as a replication origin-binding protein gene 25 for this pCMV-Luc-IRES-LT, and a base sequence that can be recognized by an LT protein that is a translation product of the LT gene is adopted as the replication origin sequence 30. Furthermore, a promoter of cytomegalovirus is adopted as a gene promoter 10 of pCMV-Luc-IRES-LT, a luciferase gene of a *photinus pyralis* (firefly) is adopted as a reporter gene 21, an IRES of encephalomyocarditis virus is adopted as an IRES 23, and a transcription termination signal sequence of bovine growth hormone gene is adopted as a transcription termination signal sequence 27.

The base sequence of the LT gene of SV40 is shown in SEQ ID NO: 1 (wild type) of the Sequence Listing. The base sequence of the LT gene does not need to be completely identical with the base sequence of SEQ ID NO: 1 as long as the function of an LT protein to initiate DNA replication is not lost. For example, a mutant-type LT gene in which an arbitrary mutation that has a possibility to enhance a function of initiating DNA replication has been introduced into the base sequence of an LT gene may be prepared and incorporated into the plasmid vector 1. Examples of the base sequence of such mutant-type LT gene are shown in SEQ ID NO: 2 (mutant-type 1), SEQ ID NO: 3 (mutant-type 2) and SEQ ID NO: 4 (mutant-type 3) in the Sequence Listing. The mutant-type LT gene according to SEQ ID NO: 2 is different from the LT gene according to SEQ ID NO: 1 in that the 319-th base guanine (G) has been substituted with adenine (A), and the 321-th base adenine (A) has been substituted with guanine (G). By this substitution of the bases, an LT protein that is a translation product of the LT gene according to SEQ ID NO: 2 is different from an LT protein of a translation product of the LT gene according to SEQ ID NO: 1 in that the 107-th amino acid glutamic acid has been substituted with lysine. The mutation is an example of a mutation in which the interaction between an LT protein and an Rb protein (a protein having a function of suppressing canceration) without impairing the DNA replication function of the LT protein. The mutant-type LT gene according to SEQ ID NO: 3 is different from the LT gene according to SEQ ID NO: 1 in that the 1206-th base thymine (T) has been substituted with guanine (G). By this substitution of the base, an LT protein that is a translation product of the LT gene according to SEQ ID NO: 3 is different from an LT protein that is a translation product of the LT gene according to SEQ ID NO: 1 in that the 402-th amino acid aspartic acid has been substituted with glutamic acid. The mutation is an example of mutation in which the interaction between an LT protein and a p53 protein (a protein having a function of suppressing canceration) is inhibited without impairing the DNA replication function of the LT protein. SEQ ID NO: 4 is a mutant-type LT gene that was prepared by introducing both the substitution of SEQ ID NO: 2 and the substitution of SEQ ID NO: 3 into the LT gene according to SEQ ID NO: 1. The above-mentioned LT genes are only examples, and the kinds and sites of the base and amino acid sequence to be substituted do not need to be identical with those of the mutant-type LT genes shown herein as long as the mutation has a possibility of enhancing a function of initiating DNA replication.

In the case when the replication origin-binding protein gene 25 is an LT gene of SV40, for example, an on sequence of SV40 is suitable as the replication origin sequence 30. An example of the on sequence of SV40 is shown in SEQ ID NO: 5 of the Sequence Listing. This base sequence also does not need to be completely identical with the base sequence of SEQ ID NO: 5 as long as the function to initiate replication is not lost.

The base sequences of the LT gene, mutant-type LT gene, the on sequence of SV40 and the like can be acquired by known genetic engineering techniques. For example, it is possible to amplify and acquire a DNA comprising a base sequence to be acquired by PCR (polymerase chain reaction) utilizing a primer set that is specific to these base sequences to be acquired. Alternatively, all of the base sequences to be acquired may be synthesized artificially. Alternatively, a base sequence that has been already incorporated in a vector may be utilized.

An example of a promoter of cytomegalovirus which is the gene promoter 10 is shown in SEQ ID NO: 6 in the Sequence Listing, an example of a luciferase gene of a *photinus pyralis* which is the reporter gene 21 is shown in SEQ ID NO: 7 in the Sequence Listing, an example of an IRES of encephalomyocarditis virus is shown in SEQ ID NO: 8 in the Sequence Listing, and an example of a transcription termination signal sequence of bos Taurus (bovine growth hormone) gene is shown in SEQ ID NO: 9 in the Sequence Listing. The plasmid vector 1 according to the present embodiment is not limited by these genes and base sequences. Furthermore, the base sequences of the genes and signals do not need to be identical with the base sequences described in the above-mentioned SEQ ID NOS as long as their functions are not lost.

2. Preparation of Vector

Next, a method for preparing the plasmid vector pCMV-Luc-IRES-LT will be explained. FIG. 3 is a drawing that schematically shows a typical flow of a method for preparing the plasmid vector pCMV-Luc-IRES-LT.

As shown in FIG. 3, a vector PGV-B2(TOYO B-Net), a vector pBSII-IRES and a vector pCMV-LT (w/oZeo) are prepared. The vector PGV-B2 includes a luciferase gene 41 of a firefly. The vector pBSII-IRES includes an IRES 43 of encephalomyocarditis virus. The vector pCMV-LT includes a gene promoter of CMV (cytomegalovirus) 45, an LT gene 47, a transcription termination signal sequence of bovine growth hormone gene 49, and an SV40 on sequence 51. The gene promoter of cytomegalovirus 45 is referred to as a CMV promoter hereinafter.

First, the PGV-B2 is digested by a restriction enzyme SacI and a restriction enzyme XbaI to cut out the luciferase gene 41. Similarly, the pBSII-IRES is cut by a restriction enzyme SacI and a restriction enzyme XbaI. Furthermore, the luciferase gene 41 that has been cut out from the PGV-B2 is linked to the pBSII-IRES that has been cut by the restriction enzyme SacI and the restriction enzyme XbaI by T4 ligase to prepare pBSII-Luc-IRES.

The pBSII-Luc-IRES is then cut by a restriction enzyme PstI. The 3'-protruding end of the pBSII-Luc-IRES that has been cut by the restriction enzyme PstI is smoothen by T4DNA polymerase. After the smoothing, a DNA fragment comprising the luciferase gene 41 and the IRES 43 is cut out from the pBSII-Luc-IRES by cutting the pBSII-Luc-IRES by a restriction enzyme NheI. Meanwhile, the pCMV-LT is also subjected to a similar treatment to that the pBSII-Luc-IRES has undergone. Namely, the pCMV-LT is cut by a restriction enzyme PstI, the 3'-protruding end is smoothen by T4DNA polymerase, and the pCMV-LT is cut by a restriction enzyme NheI. Furthermore, a DNA fragment that has been cut out from the pBSII-Luc-IRES is linked to the pCMV-LT by T4 ligase, thereby a plasmid vector pCMV-Luc-IRES-LT according to the present embodiment is prepared. By the above-mentioned treatments, the pCMV-Luc-IRES-LT comprises the CMV promoter 45, luciferase gene 41, IRES 43, LT gene 47, transcription termination signal sequence 49 and replication origin sequence 51. The luciferase gene 41, IRES 43, LT gene 47 and transcription termination signal sequence 49 are incorporated at the downstream of the CMV promoter 45.

Furthermore, pCMV-Luc-IRES-LT-E107K and pCMV-Luc-IRES-LT-D402E in which the LT gene of the above-mentioned plasmid vector pCMV-Luc-IRES-LT was recombined to form a mutant-type LT gene were prepared as other plasmid vectors 1. FIG. 4A is a drawing that schematically shows the structure of the pCMV-Luc-IRES-LT, FIG. 4B is a drawing that schematically shows the structure of the pCMV-Luc-IRES-LT-E107K, and FIG. 4C is a drawing that schematically shows the structure of the pCMV-Luc-IRES-LT-D402E. As shown in FIG. 4A, the 319-th base of the LT gene 47 of the pCMV-Luc-IRES-LT is guanine (G), the 321-th base is adenine (A), and the 1206-th base is thymine (T). As shown in FIG. 4B, the 319-th base of the LT gene 47' of the pCMV-Luc-IRES-LT-E107K is adenine (A), the 321-th base is guanine (G), and the 1206-th base is thymine (T). As shown in FIG. 4C, the 319-th base of the LT gene 47" of the pCMV-Luc-IRES-LT-D402E is guanine (G), the 321-th base is adenine (A), and the 1206-th base is guanine (G). The pCMV-Luc-IRES-LT-E107K is prepared by a site-directed mutagenesis method of a plasmid by substituting the 319-th base guanine (G) with adenine (A) and the 321-th base adenine (A) with guanine (G) in the LT gene of the pCMV-Luc-IRES-LT. The pCMV-Luc-IRES-LT-D402E is prepared by a site-directed mutagenesis method of a plasmid by substituting the 1206-th base thymine (T) with guanine (G) in the LT gene of the pCMV-Luc-IRES-LT.

This is the end of the explanation on the specific example of the method for preparing the plasmid vector 1 according to the present embodiment.

pCMV-Luc was prepared as a vector for a negative control to be introduced into a host cell together with the plasmid vector 1 or the plasmid vector 1 that has been recombined to a mutant-type LT gene. FIG. 5 is a drawing that schematically shows a typical flow of the method for preparing the vector pCMV-Luc. As shown in FIG. 5, the pCMV-Luc was prepared from pCMV-LT (w/oZeo) and a vector PGV-B2. The pCMV-LT comprises a CMV promoter 61, an LT gene 63, a transcription termination signal sequence 65 and an SV40 on sequence 67. The PGV-B2 comprises a luciferase gene 69. The pCMV-Luc can be prepared by recombining the LT gene 63 of the pCMV-LT and the luciferase gene 69 of the PGV-B2.

Specifically, at first, the PGV-B2 is cut by a restriction enzyme HindIII and a restriction enzyme XbaI to cut out the luciferase gene 69. Similarly, the pCMV-LT is cut out by the restriction enzyme HindIII and the restriction enzyme XbaI to remove the LT gene 63 from the pCMV-LT. Furthermore, a vector pCMV-Luc for a negative control is prepared by linking the luciferase gene 69 that has been cut out, to the pCMV-LT that has been cut by the restriction enzyme HindIII and the restriction enzyme XbaI, by T4 ligase. Namely, the pCMV-Luc comprises the CMV promoter 61, luciferase gene 69, transcription termination signal sequence 65 and SV40ori sequence 67. The luciferase gene 69 and transcription termination signal sequence 65 are incorporated at the downstream of the CMV promoter 61. As mentioned above, the pCMV-Luc is free from a replication origin-binding protein gene and a replication origin sequence, and thus functions as a non-self-amplified reporter vector.

3. Expression of LT Protein in Host Cell

The pCMV-Luc-IRES-LT and pCMV-Luc are introduced into a human hepatic cancer cell (Huh-7). As mentioned above, the pCMV-Luc is introduced as a vector for a negative control against the pCMV-Luc-IRES-LT.

Each plasmid vector was introduced into the cell by a lipofection method. As an introducing reagent for the plasmid vector, Lipofectamine 2000 (Life Technologies Corporation) was used. The operations for the lipofection were conducted according to the manual of the reagent. Briefly, a Lipofectamine/vector conjugate was formed by mixing 1.0 μl of a cation lipid (Lipofectamine 2000) suspended in 50 μl of Opti-MEM and 50 μl of Opti-MEM comprising 0.6 μg of the pCMV-Luc-IRES-LT or 0.4 μg of the pCMV-Luc and 0.2 μg of a DNA (pUC19). After formation of the Lipofectamine/vector composite, 50 μl of this composite liquid was added to a culture medium (Huh-7 (sown at $8.0 \times 10^4$ cells/well)) that had been cultured overnight in advance in a culture plate (a 24-well plate) to introduce the pCMV-Luc-IRES-LT into the cell.

At 48 hours after the lipofection, the culture medium was removed from the culture plate, and the cells in the culture medium were suspended in a phosphate buffer (PBS). After the suspension, the suspension liquid including the phosphate buffer and cells was centrifuged in a centrifuge at an angle velocity of 14,000 rpm over 5 minutes, and cell pellets were collected from the suspension liquid. A cell lysate for sodium dodecyl sulfate-polyacrylamide gel electrophoresis (SDS-PAGE) was added to this cell pellets, and incubation was conducted over 5 minutes in boiling water. Thereafter electrophoresis was conducted by SDS-PAGE of 8%. After the electrophoresis, the protein in the gel was blotted on a PVDF membrane by using a submarine-type blotting apparatus, and the PVDF membrane was blocked with Block Ace (Dainippon Sumitomo Pharma). After the blocking, the PVDF membrane was immersed in a primary antibody solution (a mouse anti-LT monoclonal antibody (Clone 9E10, Sigma) diluted 500-fold) and reacted at a room temperature over 1 hour. The PVDF membrane was then washed three times with tris-buffered saline (TBS).

After the washing, the amount of expression of the LT protein in the PVDF membrane was measured by using an ABC Kit (Alkaline Phosphatase Universal, VECTASTAIN). The operations of the ABC Kit were conducted according to the manual of the selling manufacturer. The PVDF membrane (an enzyme-labeled secondary antibody) was color-developed with BCIP/NBT (KPL Inc.).

Figure 6:
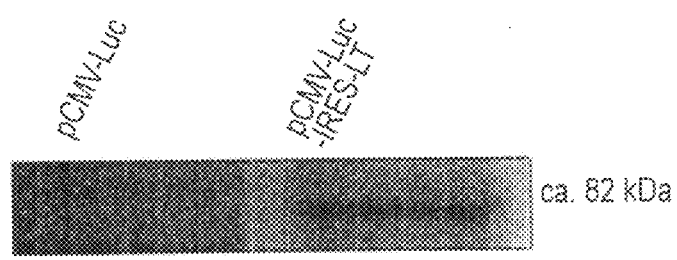
FIG. 6 is a drawing that shows the result of the detection of the amounts of expression of an LT protein in the pCMV-Luc-IRES-LT and pCMV-Luc according to examples of the present embodiment.

FIG. 6 is a drawing that shows the result of detection of the signal of the LT protein in the pCMV-Luc-IRES-LT and pCMV-Luc. As shown in FIG. 6, the expression of the LT protein was not detected in the pCMV-Luc. On the other hand, the expression of the LT protein was specifically detected in the pCMV-Luc-IRES-LT. In the example of FIG. 6, the molecular weight of the signal of the LT protein was measured to be about 82 kDa.

4. Amplification of Plasmid Vector pCMV-Luc-IRES-LT and pCMV-Luc having a same copy number were introduced into a Huh-7 cell according to a similar method to that in the above-mentioned 3. At after 72 hours from the lipofection, a DNA was extracted from the cell by using Dneasy Kit (Qiagen). The operations for extracting the DNA were conducted according to the manual of the kit. PCR was conducted by using 1.0 μl from 200 μl of the extracted DNA solution as a template to amplify the partial base sequence of the pCMV-Luc-IRES-LT or pCMV-Luc. The base sequences of the primers used in the PCR are shown below.

```
Forward primer:
                                      (SEQ ID NO: 10)
5'-CGACTGTGCCTTCTAGTTGCCAGCC-3'

Reverse primer:
                                      (SEQ ID NO: 11)
5'-CCAGCATGCCTGCTATTGTCTTCCC-3'
```

The DNA solution after the PCR reaction was subjected to electrophoresis with a 0.8% agarose gel. After the electrophoresis, the gel comprising the DNA solution was stained by ethidium bromide, and a picture of the stained gel was photographed. The staining intensity of a band drawn in the ethidium bromide-stained picture was quantified by using image analysis software (Image J).

Figure 7A:
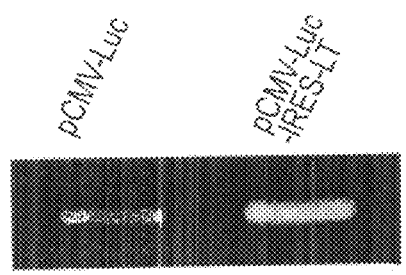
FIG. 7A is a drawing showing the result of the comparison of the copy numbers of the pCMV-Luc-IRES-LT and pCMV-Luc according to examples of the present embodiment, which shows an ethidium bromide-stained picture of the pCMV-Luc-IRES-LT and pCMV-Luc.

FIG. 7A and FIG. 7B show the result of the comparison of the copy number of the pCMV-Luc-IRES-LT (the staining intensity of the band) against the pCMV-Luc at after 72 hours from the introduction of the plasmid vector into the cell. FIG. 7A shows the ethidium bromide-stained pictures of the pCMV-Luc and pCMV-Luc-IRES-LT. FIG. 7B shows a graph (a graph of a staining intensity ratio) for the comparison of the copy numbers of the pCMV-Luc and pCMV-Luc-IRES-LT. As shown in FIG. 7A, the luminance of the picture is higher in the pCMV-Luc-IRES-LT than that in the pCMV-Luc. Therefore, it can be found from the ethidium bromide-stained picture that the pCMV-Luc-IRES-LT provides a higher signal intensity than the pCMV-Luc does. Furthermore, as shown in FIG. 7B, the pCMV-Luc-IRES-LT provides a higher signal intensity than that of the pCMV-Luc. It can be found from this graph that the copy number of the pCMV-Luc-IRES-LT has been amplified to 4.2 times of the copy number of the pCMV-Luc.

5. Reporter Gene Assay-1-(Luciferase Assay)

The pCMV-Luc-IRES-LT and pCMV-Luc having a same copy number were introduced into a Huh-7 cell and a simian kidney cancer cell (CV-1), respectively, by a lipofection method in a manner similar to that of the above-mentioned 3, and cultured on a culture plate. At 72 hours after the lipofection, the culture medium was removed from the culture plate, and each cell was washed twice with PBS, and a cell lysate that is an extraction reagent for extracting luciferase (a reporter protein) from a cell (PicaGene Cell lysis buffer LCβ, TOYO B-Net Co., Ltd.) was added thereto. The suspension liquid of the cell and cell lysate was incubated at a room temperature for 15 minutes, and the suspension liquid was then centrifuged by a centrifuge at an angle velocity of 15,000 rpm for 5 minutes to remove a cell debris from the suspension liquid. Furthermore, a luciferase substrate solution (PicaGene LT2.0, TOYO B-Net Co., Ltd.) was added to the supernatant of the suspension liquid from which the cell debris had been removed, and the luminescence intensity of the supernatant to which the luciferase substrate solution (luciferin solution) that is a detection reagent had been added was then measured by a luminometer (Mithras LB940, Berthold).

FIG. 8 is a drawing that shows the result of comparison of the signal intensities of the reporter proteins of the pCMV-Luc and pCMV-Luc-IRES-LT. As shown in FIG. 8, in the case when the host cell was Huh-7, the signal intensity of the reporter protein of the pCMV-Luc-IRES-LT against the pCMV-Luc was about 5.7 times. In the case when the host cell was CV-1, the signal intensity of the reporter protein of the pCMV-Luc-IRES-LT against the pCMV-Luc was about 19.8 times. As mentioned above, the plasmid vector according to the present embodiment can express up to about 19.8 times of a reporter protein as compared to a non-amplified plasmid vector. Therefore, the reporter gene assay according to the present embodiment can detect the activity of a gene promoter with higher sensitivity as compared to conventional reporter gene assays.

6. Reporter Gene Assay-2-(Luciferase Assay)

The pCMV-Luc-IRES-LT, pCMV-Luc-IRES-LT-E107K, pCMV-Luc-IRES-LT-D402E and pCMV-Luc having a same copy number were introduced into a simian kidney cancer cell (CV-1) by a lipofection method in a manner similar to the above-mentioned 3, and cultured on a culture plate. At 72 hours after the lipofection, the culture medium was removed from the culture plate, and each cell was washed twice with PBS, and a cell lysate that is an extraction reagent for extracting luciferase (a reporter protein) from a cell (PicaGene Cell lysis buffer LCβ, TOW B-Net Co., Ltd.) was added thereto. The suspension liquid of the cell and cell lysate was incubated at a room temperature for 15 minutes, and the suspension liquid was then centrifuged by a centrifuge at an angle velocity of 15,000 rpm for 5 minutes to remove a cell debris from the suspension liquid. Furthermore, a luciferase substrate solution (PicaGene LT2.0, TOYO B-Net Co., Ltd.) was added to the supernatant of the suspension liquid from which the cell debris had been removed, and the luminescence intensity of the supernatant to which the luciferase substrate solution (luciferin solution) that is a detection reagent had been added was then measured by a luminometer (Mithras LB940, Berthold).

FIG. 9 is a drawing that shows the result of the comparison of the signal intensities of the reporter protein of pCMV-Luc-IRES-LT, pCMV-Luc-IRES-LT-E107K and pCMV-Luc-IRES-LT-D402E against the pCMV-Luc. As shown in FIG. 10, the signal intensities of the reporter protein in the pCMV-Luc-IRES-LT, pCMV-Luc-IRES-LT-E107K and pCMV-Luc-IRES-LT-13402E against the pCMV-Luc were about 20 times, about 108 times and about 177 times, respectively. As mentioned above, the plasmid vector according to the present embodiment can express up to about 177 times of a reporter protein as compared to a non-amplified plasmid vector, by using a mutant-type LT gene. Therefore, the reporter gene assay according to the present embodiment can detect the activity of a gene promoter with higher sensitivity as compared to conventional reporter gene assays.

[Effect]

As mentioned above, the plasmid vector 1 according to the present embodiment has the gene promoter 10 to be detected, reporter gene 21, IRES 23, replication origin-binding protein gene 25, transcription termination signal sequence 27 and replication origin sequence 30. The reporter gene 21, IRES 23, replication origin-binding protein gene 25 and transcription termination signal sequence 27 are disposed at the downstream of the gene promoter 10. The IRES 23 links the reporter gene 21 to the replication origin-binding protein gene 25. Therefore, in the case when the plasmid vector 1 is introduced into a host cell that satisfies the activation condition of the gene promoter 10, a reporter protein is synthesized in the individual plasmid vector 1 while the plasmid vector 1 repeats replication in accordance with the activation of the gene promoter 10. Therefore, the plasmid vector 1 according to the present embodiment can increase more the amount of expression of a reporter protein that is synthesized due to the activity of the gene promoter 10, i.e., the amount of expression of the measured signal, as compared to a conventional non-amplified reporter vector. Furthermore, since the plasmid vector 1 according to the present embodiment utilizes a plasmid, it has no risk of infection and the like and is handled conveniently as compared to a vector utilizing a virus.

In the reporter gene assay according to the present embodiment, a host cell is cultured under a condition in which the plasmid vector 1 can be amplified in accordance with the activity of the gene promoter 10 included in the plasmid vector 1, and the amount of expression of the reporter gene 21 included in the plasmid vector 1 in the cultured host cell is measured. Therefore, the reporter gene assay according to the present embodiment can detect the activity of a gene promoter with higher sensitivity as compared to a conventional reporter gene assay that utilizes a non-amplified reporter vector.

Furthermore, the assay kit according to the present embodiment comprises the plasmid vector 1, and a reagent for detecting the expression of the reporter gene 21 included in the plasmid vector 1 in a host cell. Therefore, the assay kit according to the present embodiment can detect the activity of a gene promoter with higher sensitivity as compared to a conventional assay kit that utilizes a non-amplified reporter vector.

For example, in the case when the gene promoter 10 that is specifically activated in a cell in a pre-disease state at an early stage of a disease is incorporated in the plasmid vector 1, the amount of expression of the reporter protein per the unit number of the cell in this pre-disease state can be increased more significantly than before. By the increase in the amount of expression, the expression of the reporter protein can be detected easily, which consequently enables easy detection of the activity of the gene promoter 10. Thus, according to the present embodiment, the change in an infinitesimal quantity of a lesion cell can be detected with high sensitivity.

Thus, the present embodiment can provide a plasmid vector, a method for detecting a gene promoter and an assay kit, by which the activity of a gene promoter can be detected with high sensitivity.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for detecting the activity of a gene promoter, comprising:
   introducing a circular plasmid vector into a cell,
   culturing the cell under a condition in which the cell divides and proliferates so that the plasmid vector can be amplified in accordance with the activity of a gene promoter included in the plasmid vector, and
   measuring the amount of expression of the reporter gene included in the plasmid vector in the cultured cell,
   wherein the circular plasmid vector comprises:
   a gene promoter, which is activated in a host cell that satisfies an activation condition of the gene promoter,
   a first base sequence of a first gene that encodes a reporter protein for visualizing the activity of the gene promoter, the first base sequence functionally linked downstream of the gene promoter,
   an internal ribosome entry site that is linked downstream of the first gene,
   a second base sequence of a second gene that encodes a replication origin-binding protein, the second base sequence linked downstream of the internal ribosome entry site, wherein the second gene is a large T-antigen gene of Simian Virus 40 has the base sequence of SEQ ID NO:1, SEQ ID NO:2, SEQ ID NO:3 or SEQ ID NO:4,
   a transcription termination signal sequence for encoding a signal for terminating the transcription of the first base sequence and second base sequence, the transcription termination signal sequence linked downstream of the second base sequence, and
   a replication origin sequence that is recognized by the replication origin-binding protein, linked downstream of the transcription termination signal sequence.

2. The detection method according to claim 1, wherein the cell is a cell derived from a human or a simian.

3. The detection method according to claim 1, wherein the cell is a cell derived from a mouse or a rat.

4. The detection method according to claim 1, wherein the reporter gene is a luciferase gene, a β-galactosidase gene, a blue fluorescent protein gene, a green fluorescent protein gene or a red fluorescent protein gene, and
   the measuring comprises measuring the amount of light emission or the amount of fluorescence of a translation product of the reporter gene as the amount of expression by utilizing an optical detection apparatus.

5. The detection method according to claim 1, wherein the reporter gene is a nitric monoxide synthase gene or a xanthine oxidase gene, and
   the measuring comprises measuring the amount of active oxygen generated by a translation product of the reporter gene as the amount of expression by utilizing an electron spin resonance apparatus.

6. The detection method according to claim 1, wherein the reporter gene is a heavy metal-binding protein, and
   the measuring comprises measuring the amount of a heavy metal bound to a translation product of the reporter gene as the amount of expression by utilizing a magnetic resonance imaging apparatus, a nuclear medicine diagnostic apparatus or an X-ray computed tomographic apparatus.

7. The detection method according to claim 1, wherein the plasmid vector is self-amplified by binding of a replication origin-binding protein that is synthesized by the expression of the second gene included in the plasmid vector to a replication origin sequence included in the plasmid vector.

8. The detection method according to claim 1, wherein the cell is a cell in a pre-disease state at an early stage of a disease.

9. The detection method according to claim 1, wherein the gene promoter can be activated under a condition in which the cell divides and proliferates.

10. An assay kit, comprising:
    a circular plasmid vector and
    a reagent for detecting the expression of a gene that encodes a reporter protein included in the cyclic plasmid vector in a cell;
    wherein the circular plasmid vector comprises:
    a gene promoter, which is activated in a host cell that satisfies an activation condition of the gene promoter,
    a first base sequence of a first gene that encodes a reporter protein for visualizing the activity of the gene promoter, the first base sequence functionally linked downstream of the gene promoter,
    an internal ribosome entry site that is linked downstream of the first gene,
    a second base sequence of a second gene that encodes a replication origin-binding protein, the second base sequence linked downstream of the internal ribosome entry site, wherein the second gene is a large T-antigen gene of Simian Virus 40 has the base sequence of SEQ ID NO:1, SEQ ID NO:2, SEQ ID NO:3 or SEQ ID NO:4,
- a transcription termination signal sequence for encoding a signal for terminating the transcription of the first base sequence and second base sequence, the transcription termination signal sequence linked downstream of the second base sequence, and
- a replication origin sequence that is recognized by the replication origin-binding protein, linked downstream of the transcription termination signal sequence.

11. The assay kit according to claim 10, which further comprises a reagent for introducing the circular plasmid vector into the cell.

12. The assay kit according to claim 10, which further comprises a reagent for extracting the reporter protein from the cell.

13. The assay kit according to claim 10, wherein the first gene is a reporter gene selected from the group consisting of a luciferase gene, a β-galactosidase gene, a nitric monoxide synthase gene, a xanthine oxidase gene, a blue fluorescent protein gene, a green fluorescent protein gene, a red fluorescent protein gene, and a heavy metal-binding protein gene.

14. The assay kit according to claim 10, wherein the replication origin sequence is a replication origin sequence of Simian Virus 40.

15. The assay kit according to claim 10, wherein the large T-antigen gene has the base sequence of SEQ ID NO: 1.

16. The assay kit according to claim 10, wherein the large T-antigen gene has the base sequence of SEQ ID NO: 2, SEQ ID NO: 3 or SEQ ID NO: 4.

17. The assay kit according to claim 10, wherein the second gene is an EBNA-1 gene of Epstein-Barr virus, and the replication origin sequence is a replication origin sequence of Epstein-Barr virus.

18. The assay kit according to claim 10, wherein the replication origin sequence is a replication origin sequence of Mouse polyomavirus.

19. The assay kit according to claim 10, wherein the gene promoter is a gene promoter that is activated at an early stage of a disease, or a gene promoter that is activated in response to an environmental stimulus.

* * * * *

SEQUENCE LISTING

<160> NUMBER OF SEQ ID NOS: 11

<210> SEQ ID NO 1
<211> LENGTH: 2133
<212> TYPE: DNA
<213> ORGANISM: Simian virus 40

<400> SEQUENCE: 1

| | | | | | | |
|---|---|---|---|---|---|---|
| atggataaag | ttttaaacag | agaggaatct | ttgcagctaa | tggaccttct | aggtcttgaa | 60 |
| aggagtgcct | gggggaatat | tcctctgatg | agaaaggcat | atttaaaaaa | atgcaaggag | 120 |
| tttcatcctg | ataaaggagg | agatgaagaa | aaaatgaaga | aaatgaatac | tctgtacaag | 180 |
| aaaatggaag | atgagtaaaa | atatgctcat | caacctgact | ttggaggctt | ctgggatgca | 240 |
| actgagattc | caacctatgg | aactgatgaa | tgggagcagt | ggtggaatgc | ctttaatgag | 300 |
| gaaaacctgt | tttgctcaga | agaaatgcca | tctagtgatg | atgaggctac | tgctgactct | 360 |
| caacattcta | ctcctccaaa | aaagaagaga | aaggtagaag | accccaagga | ctttccttca | 420 |
| gaattgctaa | gttttttgag | tcatgctgtg | tttagtaata | gaactcttgc | ttgctttgct | 480 |
| atttacacca | caaaggaaaa | agctgcactg | ctatacaaga | aaattatgga | aaatattct | 540 |
| gtaacctta | taagtaggca | taacagttat | aatcataaca | tactgttttt | tcttactcca | 600 |
| cacaggcata | gagtgtctgc | tattaataac | tatgctcaaa | aattgtgtac | ctttagcttt | 660 |
| ttaatttgta | aaggggttaa | taaggaatat | ttgatgtata | gtgccttgac | tagagatcca | 720 |
| ttttctgtta | ttgaggaaag | tttgccaggt | gggttaaagg | agcatgattt | taatccagaa | 780 |
| gaagcagagg | aaactaaaca | agtgtcctgg | aagcttgtaa | cagagtatgc | aatggaaaca | 840 |
| aaatgtgatg | atgtgttgtt | attgcttggg | atgtacttgg | aatttcagta | cagttttgaa | 900 |
| atgtgtttaa | aatgtattaa | aaaagaacag | cccagccact | ataagtacca | tgaaaagcat | 960 |
| tatgcaaatg | ctgctatatt | tgctgacagc | aaaaaccaaa | aaaccatatg | ccaacaggct | 1020 |
| gttgatactg | ttttagctaa | aaagcgggtt | gatagcctac | aattaactag | agaacaaatg | 1080 |
| ttaacaaaca | gatttaatga | tcttttggat | aggatggata | taatgtttgg | ttctacaggc | 1140 |
| tctgctgaca | tagaagaatg | gatggctgga | gttgcttggc | tacactgttt | gttgcccaaa | 1200 |
| atggattcag | tggtgtatga | ctttttaaaa | tgcatggtgt | acaacattcc | taaaaaaaga | 1260 |
| tactggctgt | ttaaaggacc | aattgatagt | ggtaaaacta | cattagcagc | tgctttgctt | 1320 |
| gaattatgtg | gggggaaagc | tttaaatgtt | aatttgcct | tggacaggct | gaactttgag | 1380 |
| ctaggagtag | ctattgacca | gttttagta | gttttgagg | atgtaaaggg | cactggaggg | 1440 |
| gagtccagag | atttgccttc | aggtcaggga | attaataacc | tggacaattt | aagggattat | 1500 |
| ttggatggca | gtgttaaggt | aaacttagaa | aagaaacacc | taaataaaag | aactcaaata | 1560 |
| tttccccctg | gaatagtcac | catgaatgag | tacagtgtgc | taaaacact | gcaggccaga | 1620 |
| tttgtaaaac | aaatagattt | taggcccaga | gattatttaa | agcattgcct | ggaacgcagt | 1680 |
| gagttttgt | tagaaaagag | aataattcaa | agtggcattg | ctttgcttct | tatgttaatt | 1740 |
| tggtacagac | ctgtggctga | gtttgctcaa | agtattcaga | gcagaattgt | ggagtggaaa | 1800 |
| gagagattgg | acaaagagtt | tagtttgtca | gtgtatcaaa | aaatgaagtt | taatgtggct | 1860 |
| atgggaattg | gagttttaga | ttggctaaga | acagtgatg | atgatgatga | agacagccag | 1920 |
| gaaaatgctg | ataaaaatga | agatggtggg | gagaagaaca | tggaagactc | agggcatgaa | 1980 |
| acaggcattg | attcacagtc | ccaaggctca | tttcaggccc | ctcagtcctc | acagtctgtt | 2040 |
| catgatcata | atcagccata | ccacatttgt | agaggtttta | cttgctttaa | aaaacctccc | 2100 | acacctcccc ctgaacctga acctgaaaca taa          2133

<210> SEQ ID NO 2
<211> LENGTH: 2133
<212> TYPE: DNA
<213> ORGANISM: Simian virus 40

<400> SEQUENCE: 2

| | | | | |
|---|---|---|---|---|
| atggataaag | ttttaaacag | agaggaatct | tgcagctaa tggaccttct aggtcttgaa | 60 |
| aggagtgcct | gggggaatat | tcctctgatg | agaaaggcat atttaaaaaa atgcaaggag | 120 |
| tttcatcctg | ataaaggagg | agatgaagaa | aaaatgaaga aatgaatac tctgtacaag | 180 |
| aaaatggaag | atggagtaaa | atatgctcat | caacctgact ttggaggctt ctgggatgca | 240 |
| actgagattc | caacctatgg | aactgatgaa | tgggagcagt ggtggaatgc ctttaatgag | 300 |
| gaaaacctgt | tttgctcaaa | ggaaatgcca | tctagtgatg atgaggctac tgctgactct | 360 |
| caacattcta | ctcctccaaa | aaagaagaga | aaggtagaag accccaagga ctttccttca | 420 |
| gaattgctaa | gttttttgag | tcatgctgtg | tttagtaata gaactcttgc ttgctttgct | 480 |
| atttacacca | caaggaaaaa | agctgcactg | ctatacaaga aaattatgga aaaatattct | 540 |
| gtaacctta | taagtaggca | taacagttat | aatcataaca tactgttttt tcttactcca | 600 |
| cacaggcata | gagtgtctgc | tattaataac | tatgctcaaa aattgtgtac ctttagcttt | 660 |
| ttaatttgta | aaggggttaa | taaggaatat | ttgatgtata gtgccttgac tagagatcca | 720 |
| ttttctgtta | ttgaggaaag | tttgccaggt | gggttaaagg agcatgattt taatccagaa | 780 |
| gaagcagagg | aaactaaaca | agtgtcctgg | aagcttgtaa cagagtatgc aatggaaaca | 840 |
| aaatgtgatg | atgtgttgtt | attgcttggg | atgtacttgg aatttcagta cagttttgaa | 900 |
| atgtgtttaa | aatgtattaa | aaaagaacag | cccagccact ataagtacca tgaaaagcat | 960 |
| tatgcaaatg | ctgctatatt | tgctgacagc | aaaaaccaaa aaaccatatg ccaacaggct | 1020 |
| gttgatactg | ttttagctaa | aaagcgggtt | gatagcctac aattaactag agaacaaatg | 1080 |
| ttaacaaaca | gatttaatga | tcttttggat | aggatggata taatgtttgg ttctacaggc | 1140 |
| tctgctgaca | tagaagaatg | gatggctgga | gttgcttggc tacactgttt gttgcccaaa | 1200 |
| atggattcag | tggtgtatga | cttttttaaa | tgcatggtgt acaacattcc taaaaaaaga | 1260 |
| tactggctgt | ttaaaggacc | aattgatagt | ggtaaaacta cattagcagc tgctttgctt | 1320 |
| gaattatgtg | gggggaaagc | tttaaatgtt | aatttgcccct tggacaggct gaactttgag | 1380 |
| ctaggagtag | ctattgacca | gttttttagta | gtttttgagg atgtaaaggg cactggaggg | 1440 |
| gagtccagag | atttgccttc | aggtcaggga | attaataacc tggacaattt aagggattat | 1500 |
| ttggatggca | gtgttaaggt | aaacttagaa | aagaacacc taaataaaag aactcaaata | 1560 |
| tttccccctg | gaatagtcac | catgaatgag | tacagtgtgc ctaaaacact gcaggccaga | 1620 |
| tttgtaaaac | aaatagattt | taggcccaga | gattatttaa agcattgcct ggaacgcagt | 1680 |
| gagttttttgt | tagaaaagag | aataattcaa | agtggcattg ctttgcttct tatgttaatt | 1740 |
| tggtacagac | ctgtggctga | gtttgctcaa | agtattcaga gcagaattgt ggagtggaaa | 1800 |
| gagagattgg | acaaagagtt | tagtttgtca | gtgtatcaaa aaatgaagtt taatgtggct | 1860 |
| atgggaattg | gagttttaga | ttggctaaga | aacagtgatg atgatgatga agacagccag | 1920 |
| gaaaatgctg | ataaaatga | agatggtggg | gagaagaaca tggaagactc agggcatgaa | 1980 |
| acaggcattg | attcacagtc | ccaaggctca | tttcaggccc ctcagtcctc acagtctgtt | 2040 |

| | |
|---|---|
| catgatcata atcagccata ccacatttgt agaggtttta cttgctttaa aaaacctccc | 2100 |
| acacctcccc ctgaacctga acctgaaaca taa | 2133 |

<210> SEQ ID NO 3
<211> LENGTH: 2133
<212> TYPE: DNA
<213> ORGANISM: Simian virus 40

<400> SEQUENCE: 3

| | |
|---|---|
| atggataaag ttttaaacag agaggaatct ttgcagctaa tggaccttct aggtcttgaa | 60 |
| aggagtgcct gggggaatat tcctctgatg agaaaggcat atttaaaaaa atgcaaggag | 120 |
| tttcatcctg ataaaggagg agatgaagaa aaaatgaaga aaatgaatac tctgtacaag | 180 |
| aaaatggaag atgagtaaa atatgctcat caacctgact ttggaggctt ctggatgca | 240 |
| actgagattc caacctatgg aactgatgaa tgggagcagt ggtggaatgc ctttaatgag | 300 |
| gaaaacctgt tttgctcaga agaaatgcca tctagtgatg atgaggctac tgctgactct | 360 |
| caacattcta ctcctccaaa aaagaagaga aaggtagaaa accccaagga ctttccttca | 420 |
| gaattgctaa gttttttgag tcatgctgtg tttagtaata gaactcttgc ttgctttgct | 480 |
| atttcacca caaaggaaaa agctgcactg ctatacaaga aaattatgga aaatatttct | 540 |
| gtaacctta taagtaggca taacagttat aatcataaca tactgttttt tcttactcca | 600 |
| cacaggcata gagtgtctgc tattaataac tatgctcaaa aattgtgtac ctttagcttt | 660 |
| ttaatttgta aggggttaa taaggaatat ttgatgtata gtgccttgac tagagatcca | 720 |
| ttttctgtta ttgaggaaag tttgccaggt gggttaaagg agcatgattt taatccagaa | 780 |
| gaagcagagg aaactaaaca agtgtcctgg aagcttgtaa cagagtatgc aatggaaaca | 840 |
| aaatgtgatg atgtgttgtt attgcttggg atgtacttgg aatttcagta cagttttgaa | 900 |
| atgtgtttaa atgtattaa aaaagaacag cccagccact ataagtacca tgaaaagcat | 960 |
| tatgcaaatg ctgctatatt tgctgacagc aaaaaccaaa aaaccatatg ccaacaggct | 1020 |
| gttgatactg ttttagctaa aaagcgggtt gatagcctac aattaactag agaacaaatg | 1080 |
| ttaacaaaca gatttaatga tcttttggat aggatggata taatgtttgg ttctacaggc | 1140 |
| tctgctgaca tagaagaatg gatggctgga gttgcttggc tacactgttt gttgcccaaa | 1200 |
| atggagtcag tggtgtatga cttttttaaa tgcatggtgt acaacattcc taaaaaagaa | 1260 |
| tactggctgt ttaaaggacc aattgatagt ggtaaaacta cattagcagc tgctttgctt | 1320 |
| gaattatgtg gggggaaagc tttaaatgtt aatttgccct tggacaggct gaactttgag | 1380 |
| ctaggagtag ctattgacca gttttagta gttttgagg atgtaaaggg cactggaggg | 1440 |
| gagtccagag atttgccttc aggtcaggga attaataacc tggacaattt aagggattat | 1500 |
| ttggatggca gtgttaaggt aaacttagaa aagaaacacc taaataaaag aactcaaata | 1560 |
| tttccccctg aatagtcac catgaatgag tacagtgtgc ctaaaacact gcaggccaga | 1620 |
| tttgtaaaac aaatagattt taggcccaga gattatttaa agcattgcct ggaacgcagt | 1680 |
| gagtttttgt tagaaaagag aataattcaa agtggcattg ctttgcttct tatgttaatt | 1740 |
| tggtacagac ctgtggctga gtttgctcaa gtattcaga gcagaattgt ggagtggaaa | 1800 |
| gagagattgg acaaagagtt tagtttgtca gtgtatcaaa aaatgaagtt taatgtggct | 1860 |
| atgggaattg gagttttaga ttggctaaga acagtgatg atgatgatga agacagccag | 1920 |
| gaaaatgcta taaaaatga agatggtggg gagaagaaca tggaagactc agggcatgaa | 1980 |
| acaggcattg attcacagtc ccaaggctca tttcaggccc ctcagtcctc acagtctgtt | 2040 |

| | |
|---|---|
| catgatcata atcagccata ccacatttgt agaggtttta cttgctttaa aaaacctccc | 2100 |
| acacctcccc ctgaacctga acctgaaaca taa | 2133 |

<210> SEQ ID NO 4
<211> LENGTH: 2133
<212> TYPE: DNA
<213> ORGANISM: Simian virus 40

<400> SEQUENCE: 4

| | |
|---|---|
| atggataaag ttttaaacag agaggaatct ttgcagctaa tggaccttct aggtcttgaa | 60 |
| aggagtgcct gggggaatat tcctctgatg agaaaggcat atttaaaaaa atgcaaggag | 120 |
| tttcatcctg ataaaggagg agatgaagaa aaaatgaaga aaatgaatac tctgtacaag | 180 |
| aaaatggaag atgagtaaa atatgctcat caacctgact ttggaggctt ctgggatgca | 240 |
| actgagattc aacctatgg aactgatgaa tgggagcagt ggtggaatgc ctttaatgag | 300 |
| gaaaacctgt tttgctcaaa ggaaatgcca tctagtgatg atgaggctac tgctgactct | 360 |
| caacattcta ctcctccaaa aagaagaga aaggtagaag accccaagga cttttccttca | 420 |
| gaattgctaa gttttttgag tcatgctgtg tttagtaata aactcttgc ttgctttgct | 480 |
| atttacacca caaaggaaaa agctgcactg ctatacaaga aaattatgga aaaatattct | 540 |
| gtaaccttta taagtaggca taacagttat aatcataaca tactgttttt tcttactcca | 600 |
| cacaggcata gagtgtctgc tattaataac tatgctcaaa aattgtgtac ctttagcttt | 660 |
| ttaatttgta aaggggttaa taaggaatat ttgatgtata gtgccttgac tagagatcca | 720 |
| ttttctgtta ttgaggaaag tttgccaggt gggttaaagg agcatgattt taatccagaa | 780 |
| gaagcagagg aaactaaaca agtgtcctgg aagcttgtaa cagagtatgc aatggaaaca | 840 |
| aaatgtgatg atgtgttgtt attgcttggg atgtacttgg aatttcagta cagttttgaa | 900 |
| atgtgtttaa aatgtattaa aaagaacag cccagccact ataagtacca tgaaaagcat | 960 |
| tatgcaaatg ctgctatatt tgctgacagc aaaaaccaaa aaccatatg ccaacaggct | 1020 |
| gttgatactg ttttagctaa aaagcgggtt gatagcctac aattaactag agaacaaatg | 1080 |
| ttaacaaaca gatttaatga tcttttggat aggatggata taatgtttgg ttctacaggc | 1140 |
| tctgctgaca tagaagaatg gatggctgga gttgcttggc tacactgttt gttgcccaaa | 1200 |
| atggagtcag tggtgtatga ctttttaaaa tgcatggtgt acaacattcc taaaaaaaga | 1260 |
| tactggctgt ttaaggacc aattgatagt ggtaaaacta cattagcagc tgctttgctt | 1320 |
| gaattatgtg gggggaaagc tttaaatgtt aatttgccct tggacaggct gaactttgag | 1380 |
| ctaggagtag ctattgacca gtttttagta gttttttgagg atgtaaaggg cactggaggg | 1440 |
| gagtccagag atttgccttc aggtcaggga attaataacc tggacaattt aagggattat | 1500 |
| ttggatggca gtgttaaggt aaacttagaa agaaacacc taaataaaag aactcaaata | 1560 |
| tttcccctg aatagtcac catgaatgag tacagtgtgc ctaaaacact gcaggccaga | 1620 |
| tttgtaaaac aaatagattt taggcccaga gattatttaa agcattgcct ggaacgcagt | 1680 |
| gagtttttgt tagaaaagag aataattcaa agtggcattg ctttgcttct tatgttaatt | 1740 |
| tggtacagac ctgtggctga gtttgctcaa agtattcaga gcagaattgt ggagtggaaa | 1800 |
| gagagattgg acaaagagtt tagtttgtca gtgtatcaaa aatgaagtt taatgtggct | 1860 |
| atgggaattg gagttttaga ttggctaaga aacagtgatg atgatgatga agacagccag | 1920 |
| gaaaatgctg ataaaaatga agatggtggg gagaagaaca tggaagactc agggcatgaa | 1980 |

| | |
|---|---|
| acaggcattg attcacagtc ccaaggctca tttcaggccc ctcagtcctc acagtctgtt | 2040 |
| catgatcata atcagccata ccacatttgt agaggtttta cttgctttaa aaaacctccc | 2100 |
| acacctcccc ctgaacctga acctgaaaca taa | 2133 |

<210> SEQ ID NO 5
<211> LENGTH: 165
<212> TYPE: DNA
<213> ORGANISM: Simian virus 40

<400> SEQUENCE: 5

| | |
|---|---|
| gctagcaata aaatatcttt attttcatta catctgtgtg ttggttttttt gtgtgaatcg | 60 |
| atagtactaa catacgctct ccatcaaaac aaaacgaaac aaaacaaact agcaaaatag | 120 |
| gctgtcccca gtgcaagtgc aggtgccaga acatttctcg ctagc | 165 |

<210> SEQ ID NO 6
<211> LENGTH: 654
<212> TYPE: DNA
<213> ORGANISM: Cytomegarovirus (CMV)

<400> SEQUENCE: 6

| | |
|---|---|
| cgatgtacgg gccagatata cgcgttgaca ttgattattg actagttatt aatagtaatc | 60 |
| aattacgggg tcattagttc atagcccata tatggagttc cgcgttacat aacttacggt | 120 |
| aaatggcccg cctggctgac cgcccaacga ccccccgccca ttgacgtcaa taatgacgta | 180 |
| tgttcccata gtaacgccaa tagggacttt ccattgacgt caatgggtgg agtatttacg | 240 |
| gtaaactgcc cacttggcag tacatcaagt gtatcatatg ccaagtacgc ccctattga | 300 |
| cgtcaatgac ggtaaatggc ccgcctggca ttatgcccag tacatgacct tatgggactt | 360 |
| tcctacttgg cagtacatct acgtattagt catcgctatt accatggtga tgcggttttg | 420 |
| gcagtacatc aatgggcgtg gatagcggtt tgactcacgg ggatttccaa gtctccaccc | 480 |
| cattgacgtc aatgggagtt tgttttggca ccaaaatcaa cgggactttc caaaatgtcg | 540 |
| taacaactcc gccccattga cgcaaatggg cggtaggcgt gtacggtggg aggtctatat | 600 |
| aagcagagct ctctggctaa ctagagaacc cactgcttac tggcttatcg aaat | 654 |

<210> SEQ ID NO 7
<211> LENGTH: 1653
<212> TYPE: DNA
<213> ORGANISM: Photinus pyralis

<400> SEQUENCE: 7

| | |
|---|---|
| atggaagacg ccaaaaacat aaagaaaggc ccggcgccat tctatccgct ggaagatgga | 60 |
| accgctggag agcaactgca taaggctatg aagagatacg ccctggttcc tggaacaatt | 120 |
| gcttttacag atgcacatat cgaggtggac atcacttacg ctgagtactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgggcatt | 360 |
| tcgcagccta ccgtggtgtt cgtttccaaa aggggttgc aaaaaatttt gaacgtgcaa | 420 |
| aaaaagctcc caatcatcca aaaaattatt atcatggatt ctaaaacgga ttaccaggga | 480 |
| tttcagtcga tgtacacgtt cgtcacatct catctacctc ccggttttaa tgaatacgat | 540 |
| tttgtgccag agtccttcga tagggacaag acaattgcac tgatcatgaa ctcctctgga | 600 |
| tctactggtc tgcctaaagg tgtcgctctg cctcatagaa ctgcctgcgt gagattctcg | 660 |

```
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttc tgaggagcct tcaggattac    840
aagattcaaa gtgcgctgct ggtgccaacc ctattctcct tcttcgccaa aagcactctg    900
attgacaaat acgatttatc taatttacac gaaattgctt ctggtggcgc tcccctctct    960
aaggaagtcg gggaagcggt tgccaagagg ttccatctgc caggtatcag gcaaggatat   1020
gggctcactg agactacatc agctattctg attacacccg aggggatga taaaccgggc   1080 gcggtcggta agttgttcc attttttgaa gcgaaggttg tggatctgga taccgggaaa    1140
acgctgggcg ttaatcaaag aggcgaactg tgtgtgagag gtcctatgat tatgtccggt   1200
tatgtaaaca atccggaagc gaccaacgcc ttgattgaca aggatggatg ctacattct    1260 ggagacatag cttactggga cgaagacgaa cacttcttca tcgttgaccg cctgaagtct   1320
ctgattaagt acaaaggcta tcaggtggct cccgctgaat tggaatccat cttgctccaa   1380
caccccaaca tcttcgacgc aggtgtcgca ggtcttcccg acgatgacgc cggtgaactt   1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aagtcttac cggaaaaactc gacgcaagaa aaatcagaga gatcctcata   1620
aaggccaaga agggcggaaa gatcgccgtg taa                                1653

<210> SEQ ID NO 8
<211> LENGTH: 599
<212> TYPE: DNA
<213> ORGANISM: Encephalomyocarditis virus

<400> SEQUENCE: 8
cctctagcgg gatcaattcc gcccccccc cctaacgtta ctggccgaag ccgcttggaa     60
taaggccggt gtgcgtttgt ctatatgtta ttttccacca tattgccgtc ttttggcaat   120
gtgagggccc ggaaacctgg ccctgtcttc ttgacgagca ttcctagggg tctttccccct   180 ctcgccaaag gaatgcaagg tctgttgaat gtcgtgaagg aagcagttcc tctggaagct   240
tcttgaagac aaacaacgtc tgtagcgacc ctttgcaggc agcggaaccc cccacctggc   300
gacaggtgcc tctgcggcca aaagccacgt gtataagata cacctgcaaa ggcggcacaa   360
ccccagtgcc acgttgtgag ttggatagtt gtggaaagag tcaaatggct ctcctcaagc   420
gtattcaaca aggggctgaa ggatgcccag aaggtacccc attgtatggg atctgatctg   480
gggcctcggt gcacatgctt tacgtgtgtt tagtcgaggt taaaaaacgt ctaggccccc   540
cgaaccacgg ggacgtggtt ttcctttgaa aaacacgata taccatgat tgaacaaga    599

<210> SEQ ID NO 9
<211> LENGTH: 228
<212> TYPE: DNA
<213> ORGANISM: Bos taurus

<400> SEQUENCE: 9
gtttaaaccc gctgatcagc ctcgactgtg ccttctagtt gccagccatc tgttgtttgc     60 ccctccccg tgccttcctt gaccctggaa ggtgccactc ccactgtcct ttcctaataa    120
aatgaggaaa ttgcatcgca ttgtctgagt aggtgtcatt ctattctggg gggtggggtg    180
gggcaggaca gcaaggggga ggattgggaa gacaatagca ggcatgct                 228
```

```
<210> SEQ ID NO 10
<211> LENGTH: 25
<212> TYPE: DNA
<213> ORGANISM: Artificial Sequence
<220> FEATURE:
<223> OTHER INFORMATION: Synthetic primer

<400> SEQUENCE: 10
cgactgtgcc ttctagttgc cagcc                                      25

<210> SEQ ID NO 11
<211> LENGTH: 25
<212> TYPE: DNA
<213> ORGANISM: Artificial Sequence
<220> FEATURE:
<223> OTHER INFORMATION: Synthetic primer

<400> SEQUENCE: 11
ccagcatgcc tgctattgtc ttccc                                      25
```